(12) United States Patent
Stadler

(10) Patent No.: US 6,787,539 B2
(45) Date of Patent: Sep. 7, 2004

(54) 2,4,5,-TRISUBSTITUTED PYRIMIDINE DERIVATIVES

(75) Inventor: Heinz Stadler, Rheinfelden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 101 days.

(21) Appl. No.: 09/977,586

(22) Filed: Oct. 15, 2001

(65) Prior Publication Data

US 2002/0099207 A1 Jul. 25, 2002

(30) Foreign Application Priority Data

Nov. 22, 2000 (EP) .............................................. 00125529

(51) Int. Cl.$^7$ ..................... C07D 239/24; C07D 413/04; C07D 417/04; C07D 403/04; A61K 31/505

(52) U.S. Cl. ................. 514/227.8; 514/231.5; 514/269; 514/273; 514/274; 544/60; 544/123; 544/295; 544/296; 544/314; 544/318; 544/321; 544/323; 544/324; 544/325

(58) Field of Search ........................... 544/60, 123, 295, 544/296, 314, 318, 321, 323, 326, 325; 514/227.8, 231.5, 269, 273, 274

(56) References Cited

U.S. PATENT DOCUMENTS 5,972,938 A 10/1999 Rupniak et al. ......... 514/236.2

FOREIGN PATENT DOCUMENTS

| EP | 0257 102 | 3/1988 |
| WO | WO 95/16679 | 6/1995 |
| WO | WO 95/18124 | 7/1995 |
| WO | WO 95/23798 | 9/1995 |
| WO | WO 01/57025 | 8/2001 |
| WO | WO-01/057025 A1 * | 8/2001 |

OTHER PUBLICATIONS

Barker, *Reviews in Neuroscience.*, vol. 7(3),pp. 187–214 (1996).
Longmore et al., *Can. J. Physiol.*, vol. 75, pp. 612–621 (1997).
Kramer et al., *Science*, vol. 281, pp.1640–1645 (1998).
Maggi et al., *J. Auton. Pharmacol.*, vol. 13, pp. 23–93 (1993).
Navari et al., *New England J. of Medicine*, vol. 340(3), pp. 190–195 (1999).
Maggi et al., *Neuropeptides*, vol. 32(1), pp. 1–49 (1998).
Doi et al., *Eur. J. of Pharmacology.*, vol. 383, pp. 297–303 (1999).
Palma et al., *Life Sciences*, vol. 67, pp. 985–1001 (2000).
Murta et al., *Nature*, vol. 405, pp. 180–183 (2000).

Nimmo et al., *Neurokinin 1 (NK–1) Receptor Antagonists Improve the Neurological Outcome Following Traumatic Brain Injury*, Abstract of Paper presented at the International Tachykinin Conference 2000 in La Grande Motte, France, Oct. 17–20, 2000.

* cited by examiner

Primary Examiner—Venkataraman Balasubramanian
(74) Attorney, Agent, or Firm—George W. Johnston; Patricia S. Rocha-Tramaloni; Kimberly J. Prior

(57) ABSTRACT

The invention relates to compounds of the formula

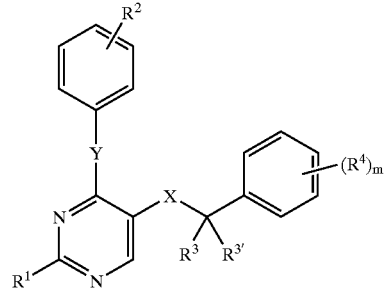

wherein
$R^1$ is lower alkyl, lower alkoxy, pyridinyl, pyrimidinyl, phenyl, —S-lower alkyl, —S(O)$_2$-lower alkyl, —N(R)—(CH$_2$)$_n$—N(R)$_2$, —O—(CH$_2$)$_n$—N(R)$_2$, —N(R)$_2$, or a cyclic tertiary amine of the group

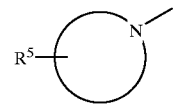

which may contain one additional heteroatom, selected from N, O or S, and wherein this group may be connected with the pyrimidine ring via the linker —O(CH$_2$)$_n$—;
$R^2$ is hydrogen, lower alkyl, lower alkoxy, halogen or trifluoromethyl;
$R^3/R^{3'}$ is, independently from each other, hydrogen or lower alkyl;
$R^4$ is independently from each other halogen, trifluoromethyl or lower alkoxy;
$R^5$ is hydrogen or lower alkyl;
R is, independently from each other, hydrogen or lower alkyl;
X is —C(O)N(R)— or —N(R)C(O)—;
Y is —O—, —S—, —SO$_2$—, - or —N(R)—;
n is 1,2,3 or 4; and
m is 0,1 or 2;
or a pharmaceutically acceptable acid addition salt thereof. The compound of the invention has affinity to the NK1 receptor and is therefore suitable in the treatment of diseases related to this recepor.

20 Claims, No Drawings

2,4,5,-TRISUBSTITUTED PYRIMIDINE DERIVATIVES

FIELD OF INVENTION

The compound of the invention has activity in biological systems and more particularly has activity as an antagonist to neurokinin 1 receptors.

BACKGROUND

The neuropeptide receptor for substance P (NK-1) is widely distributed throughout the mammalian nervous system (especially brain and spinal ganglia), the circulatory system and peripheral tissues (especially the duodenum and jejunum) and are involved in regulating a number of diverse biological processes.

The central and peripheral actions of the mammalian tachykinin substance P have been associated with numerous inflammatory conditions including migraine, rheumatoid arthritis, asthma, and inflammatory bowel disease as well as mediation of the emetic reflex and the modulation of central nervous system (CNS) disorders such as Parkinson's disease (Neurosci. Res., 1996, 7, 187–214), anxiety (Can. J. Phys., 1997, 75, 612–621) and depression (Science, 1998, 281, 1640–1645).

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases reviewed in "Tachykinin Receptor and Tachykinin Receptor Antagonists", J. Auton. Pharmacol., 13, 23–93, 1993.

Furthermore, Neurokinin 1 receptor antagonists are being developed for the treatment of a number of physiological disorders associated with an excess or imbalance of tachykinin, in particular substance P. Examples of conditions in which substance P has been implicated include disorders of the central nervous system such as anxiety, depression and psychosis (WO 95/16679, WO 95/18124 and WO 95/23798).

The neurokinin-1 receptor antagonists are further useful for the treatment of motion sickness and for treatment induced vomiting.

In addition, in The New England Journal of Medicine, Vol. 340, No. 3 190–195, 1999 has been described the reduction of cisplatin-induced emesis by a selective neurokinin-1-receptor antagonist.

Furthermore, U.S. Pat. No. 5,972,938 describes a method for treating a psychoimmunologic or a psychosomatic disorder by administration of a tachykinin receptor, such as NK-1 receptor antagonist.

The usefulness of neurokinin 1 receptor antagonists for the treatment of certain forms of urinary incontinence is further described in "Neuropeptides, 32(1), 1–49, (1998)" and "Eur. J. Pharmacol., 383(3), 297–303, (1999)".

Life Sci., (2000), 67(9), 985–1001 describes, that astrocytes express functional receptors to numerous neurotransmitters including substance P, which is an important stimulus for reactive astrocytes in CNS development, infection and injury. In brain tumors malignant glial cells originating from astrocytes are triggered by tachykinins via NK-1 receptors to release soluble mediators and to increase their proliferative rate. Therefore, selective NK-1 receptor antagonists may be useful as a therapeutic approach to treat malignant gliomas in the treatment of cancer.

A paper in Nature (London) (2000), 405(6783), 180–183 describes that mice with a genetic disruption of NK-1 receptor show a loss of the rewarding properties of morphine. Consequently NK-1 receptor antagonists may be useful in the treatment of withdrawal symptoms of addictive drugs such as opiates and nicotine and reduction of their abuse/craving.

NK1 receptor antagonists have been reported to have also a beneficial effect in the therapy of traumatic brain injury (Paper presented by Prof. Nimmo at the International Tachykinin Conference 2000 in La Grande Motte, France, Oct. 17–20, 2000 with the title "Neurokinin 1 (NK-1) Receptor Antagonists Improve the Neurological Outcome Following Traumatic Brain Injury" (Authors: A. J. Nimnmo, C. J. Bennett, X. Hu, I. Cernak, R. Vink).

The compounds of the present invention are further useful for the treatment of benign prostatic hyperplasia (BPH), which is common in older men. BPH can be progressive and lead to urinary retention, infections, bladder calculi and renal failure. This indication has been reported in EP 01109853.0.

SUMMARY

The present invention is a compound of the formula

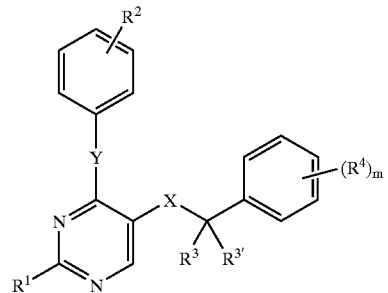

I wherein
$R^1$ is lower alkyl, lower alkoxy, pyridinyl, pyrimidinyl, phenyl, —S-lower alkyl, —S(O)$_2$-lower alkyl, —N(R$^a$)—(CH$_2$)$_n$—N(R$^b$)$_2$, —O—(CH$_2$)$_n$—N(R$^c$)$_2$, —N(R$^d$)$_2$, or a cyclic tertiary amine of the group

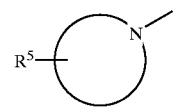

or a cyclic tertiary amine of the group

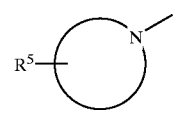

that contains one additional heteroatom, selected from N, O or S, said cyclic tertiary amine being connected to a pyrimidine ring of formula 1 or connected to said pyrimidine ring via the linker —O(CH$_2$)$_n$—;

$R^2$ is hydrogen, lower alkyl, lower alkoxy, halogen or trifluoromethyl;

$R^3/R^{3'}$ are, independently from each other, hydrogen or lower alkyl;

$(R^4)_m$ are, independently from each other in the case where m is not 0 or 1, halogen, trifluoromethyl or lower alkoxy;

$R^5$ is hydrogen or lower alkyl;

R, $R^a$, $R^b$, $R^c$, $R^d$, $R^e$, $R^f$ are, independently from each other, hydrogen or lower alkyl;

X is —C(O)N($R^e$)— or —N($R^f$)C(O)—;

Y is —O—, —S—, —SO$_2$—, or —N(R)—;

n is 1,2,3 or 4; and m is 0, 1 or 2;

and a pharmaceutically acceptable acid addition salt thereof.

The compounds of formula I and their salts are characterized by valuable therapeutic properties. It has been surprisingly found that the compounds of the present invention are antagonists of the Neurokinin 1 (NK-1, substance P) receptor. Substance P is a naturally occurring undecapeptide belonging to the tachykinin family of peptides, the latter being so-named because of their prompt contractile action on extravascular smooth muscle tissue. The receptor for substance P is a member of the superfamily of G protein-coupled receptors.

The compounds of the present invention are further useful for the treatment of benign prostatic hyperplasia (BPH), which is common in older men. BPH can be progressive and lead to urinary retention, infections, bladder calculi and renal failure. This indication has been reported in EP 01109853.0.

The compounds of formula I can also be used in the form of their prodrugs, for example in form of their N-oxides. The prodrugs may add to the value of the present compounds advantages in adsorption, pharmacokinetics in distribution and transport to the brain.

Objects of the present invention are the compounds of formula I and pharmaceutically acceptable salts thereof, the preparation of the above-mentioned compounds, medicaments containing them and their manufacture as well as the use of the above-mentioned compounds in the control or prevention of illnesses, especially of illnesses and disorders of the kind referred to earlier or in the manufacture of corresponding medicaments.

DETAILED DESCRIPTION

As used herein, the term "lower alkyl" denotes a saturated straight- or branched-chain alkyl group containing from 1 to 7 carbon atoms, for example, methyl, ethyl, propyl, isopropyl, n-butyl, i-butyl, 2-butyl, t-butyl and the like. Preferred lower alkyl groups are groups with 1–4 carbon atoms.

The term "halogen" denotes chlorine, iodine, fluorine and bromine.

The term "lower alkoxy" denotes a group wherein the alkyl residue is as defined above, and which is attached via an oxygen atom.

As used in this disclosure, the term "cyclic tertiary amine" denotes a five or six membered heterocylic ring moiety, having at least one N atom which is always connected to the pyrimidine ring of formula I, or a five or six membered heterocylic ring moiety with one nitrogen atom which is always connected to the pyrimidine ring of formula I having one additional N, O or S atom, including but not limited to, for example, pyrrolidinyl, imidazolidinyl, pyrazolidinyl, piperidinyl, piperazinyl, morpholinyl, thiomorpholinyl, thiomorpholin-1,1-dioxo or thiomorpholin-1-oxo and the like.

The term "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The most preferred indications in accordance with the present invention are those, which include disorders of the central nervous system, for example the treatment or prevention of certain depressive disorders or emesis by the administration of NK-1 receptor antagonists. A major depressive episode has been defined as being a period of at least two weeks during which, for most of the day and nearly every day, there is either depressed mood or the loss of interest or pleasure in all, or nearly all activities.

Preferred are compounds of formula I, in which X is —C(O)N(CH$_3$)-and Y is —O—.

Exemplary preferred compounds of this group are those, wherein $R^1$ is a cyclic tertiary amine, for example the following compounds:

2-(4-methyl-piperazin-1-yl)-4-o-tolyloxy-pyrimidine-5-carboxylic acid (3,5-bis-trifluoromethyl-benzyl)-methyl-amide, 2-piperazin-1-yl-4-o-tolyloxy-pyrimidine-5-carboxylic acid (3,5-bis-trifluoromethyl-benzyl)-methyl-amide or 4-(2-chloro-phenoxy)-2-(4-methyl-piperazin-1-yl)-pyrimidine-5-carboxylic acid (3,5-bis-trifluoromethyl-benzyl)-methyl-amide.

Further preferred compounds of the above mentioned group are those, wherein $R^1$ is —O—(CH$_2$)$_n$-cyclic tertiary amine or the group —O—(CH$_2$)—NR$_2$. Such compounds are 2-(2-morpholin-4-yl-ethoxy)-4-o-tolyloxy-pyrimidine-5-carboxylic acid (3,5-bis-trifluoromethyl-benzyl)-methyl-amide or 2-(2-dimethylamino-ethoxy)-4-o-tolyloxy-pyrimidine-5-carboxylic acid (3,5-bis-trifluoromethyl-benzyl)-methyl-amide.

Further preferred are compounds of formula I, in which X is —N(CH$_3$)C(O)— and Y is —O—. Exemplary preferred compounds of this group are those, wherein $R^1$ is —S-lower alkyl, for example the following compounds:

2-(3,5-bis-trifluoromethyl-phenyl)-N-methyl-N-(2-methylsulfanyl-4-o-tolyloxy-pyrimidin-5-yl)-isobutyramide, 2-(3,5-bis-trifluoromethyl-phenyl)-N-[4-(4-fluoro-phenoxy)-2-methylsulfanyl-pyrimidin-5-yl]-N-methyl-isobutyramide or 2-(3,5-bis-trifluoromethyl-phenyl)-N-[4-(2-chloro-phenoxy)-2-methylsulfanyl-pyrimidin-5-yl]-N-methyl-isobutyramide.

Further preferred compounds of the above group are those, wherein $R^1$ is a cyclic tertiary amine, for example the following compounds:

2-(3,5-bis-trifluoromethyl-phenyl)-N-methyl-N-(2-morpholin-4-yl-4-o-tolyloxy-pyrimidin-5-yl)-isobutyramide, 2-(3,5-bis-trifluoromethyl-phenyl)-N-methyl-N-[2-(4-methyl-piperazin-1-yl)-4-o-tolyloxy-pyrimidin-5-yl]-isobutyramide, 2-(3,5-bis-trifluoromethyl-phenyl)-N-methyl-N-(2-piperazin-1-yl-4-o-tolyloxy-pyrimidin-5-yl)-isobutyramide, 2-(3,5-bis-trifluoromethyl-phenyl)-N-[4-(4-fluoro-phenoxy)-2-(4-methyl-piperazin-1-yl)-pyrimidin-5-yl]-N-methyl-isobutyramide,
2-(3,5-bis-trifluoromethyl-phenyl)-N-[4-(4-fluoro-phenoxy)-2-piperazin-1-yl-pyrimidin-5-yl]-N-methyl-isobutyramide,
2-(3,5-bis-trifluoromethyl-phenyl)-N-[4-(2-chloro-phenoxy)-2-morpholin-4-yl-pyrimidin-5-yl]-N-methyl-isobutyramide,
2-(3,5-bis-trifluoromethyl-phenyl)-N-[4-(2-chloro-phenoxy)-2-(4-methyl-piperazin-1-yl)-pyrimidin-5-yl]-N-methyl-isobutyramide or
2-(3,5-Bis-trifluoromethyl-phenyl)-N-[4-(2-chloro-phenoxy)-2-piperazin-1-yl-pyrimidin-5-yl]-N-methyl-isobutyramide.

Preferred compounds of this group are further those, wherein $R^1$ is $-N(R^a)(CH_2)_n NR^b_2$, for example the following compounds:
2-(3,5-bis-trifluoromethyl-phenyl)-N-[2-(2-dimethylamino-ethylamino)-4-o-tolyloxy-pyrimidin-5-yl]-N-methyl-isobutyramide or
2-(3,5-bis-trifluoromethyl-phenyl)-N-[2-(2-dimethylamino-ethylamino)-4-(4-fluoro-phenoxy)-pyrimidin-5-yl]-N-methyl-isobutyramide.

Further preferred compounds of this group are those, wherein $R^1$ is $-O(CH_2)_n$-cyclic tertiary amine or the group $-O(CH_2)_n NR^c_2$, for example the following compounds:
2-(3,5-bis-trifluoromethyl-phenyl)-N-methyl-N-[2-(2-morpholin-4-yl-ethoxy)-4-o-tolyloxy-pyrimidin-5-yl]-isobutyramide,
2-(3,5-bis-trifluoromethyl-phenyl)-N-[4-(2-chloro-phenoxy)-2-(2-morpholin-4-yl-ethoxy)-pyrimidin-5-yl]-N-methyl-isobutyramide,
2-(3,5-bis-trifluoromethyl-phenyl)-N-[2-(2-dimethylamino-ethoxy)-4-o-tolyloxy-pyrimidin-5-yl]-N-methyl-isobutyramide,
2-(3,5-bis-trifluoromethyl-phenyl)-N-[2-(3-dimethylamino-propoxy)-4-o-tolyloxy-pyrimidin-5-yl]-N-methyl-isobutyramide,
2-(3,5-bis-trifluoromethyl-phenyl)-N-[2-(2-dimethylamino-ethoxy)-4-(4-fluoro-phenoxy)-pyrimidin-5-yl]-N-methyl-isobutyramide,
2-(3,5-bis-trifluoromethyl-phenyl)-N-[2-(3-dimethylamino-propoxy)-4-(4-fluoro-phenoxy)-pyrimidin-5-yl]-N-methyl-isobutyramide,
2-(3,5-bis-trifluoromethyl-phenyl)-N-[2-(2-dimethylamino-ethoxy)-4-(2-chloro-phenoxy)-pyrimidin-5-yl]-N-methyl-isobutyramide or
2-(3,5-bis-trifluoromethyl-phenyl)-N-[2-(3-dimethylamino-propoxy)-4-(2-chloro-phenoxy)-pyrimidin-5-yl]-N-methyl-isobutyramide.

Also preferred is a compound of formula I wherein X is $-C(O)N(R^e)-$, wherein $R^e$ is lower alkyl, Y is $-O-$ and $R^2$ is lower alkyl. Yet another preferred compound of formula I is a compound wherein X is $-C(O)N(R^e)-$, wherein $(R^e)-$ is hydrogen, $R^2$ is lower alkyl and Y is $-O-$. A further preferred compound of formula 1 is wherein X is $-C(O)NR^e-$, wherein $R^e$ is lower alkyl, Y is $-O-$, and $R^2$ is hydrogen. An additional preferred compound of formula I is wherein X is $-C(O)N(R^e)-$ wherein $R^e$ is lower alkyl, Y is $-O-$ and $R^2$ is halogen. Yet another additional preferred compound of formula I is wherein X is $-C(O)N(R^e)-$ wherein $R^e$ is lower alkyl, Y is $-O-$ and $R^2$ is lower alkoxy. Another preferred compound of formula I is wherein X is $-N(R^f)C(O)-$ wherein $R^f$ is lower alkyl, Y is $-O-$ and $R^2$ is lower alkyl. Yet another preferred compound of formula I is wherein X is $-N(R^f)C(O)-$ wherein $R^f$ is lower alkyl, Y is $-O-$ and $R^2$ is halogen.

The present compound of formula I and pharmaceutically acceptable salts thereof can be prepared by methods known in the art, for example, by processes described below, which process comprises reacting a compound of formula

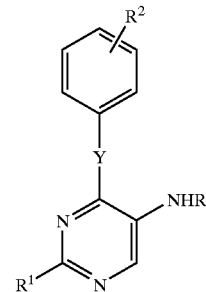

II with a compound of formula

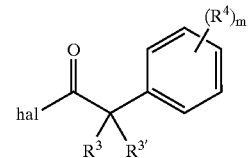

III to a compound of formula

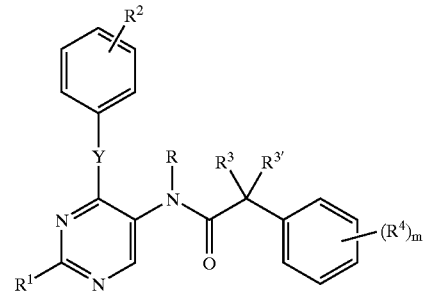

Ia wherein Y, $R^1$, $R^2$, $R^3$, $R^{3'}$, $R^4$, R (for the purposes of these reaction schemes, the designation "R" includes R, $R^a$, $R^b$, $R^c$, $R^d$, $R^e$, $R^f$) and m have the significances given above, or reacting a compound of formula

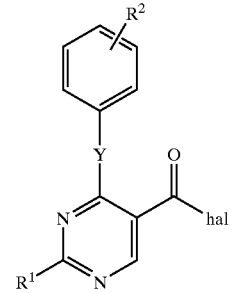

IV with a compound of formula

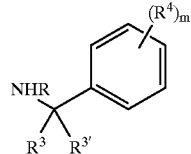

to give a compound of formula

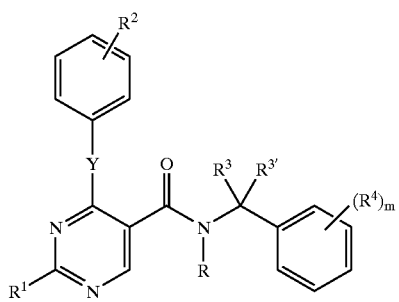

Ib wherein Y, R¹, R², R³, R³', R⁴, R (for the purposes of these reaction schemes, the designation "R" includes R, $R^a$, $R^b$, $R^c$, $R^d$, R, $R^f$) and m have the significances given above, or reacting a compound of formula

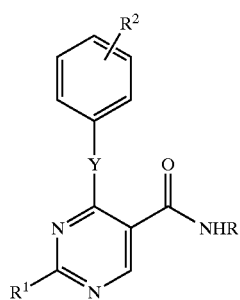

VI with a compound of formula

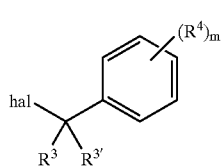

VII to a compound of formula

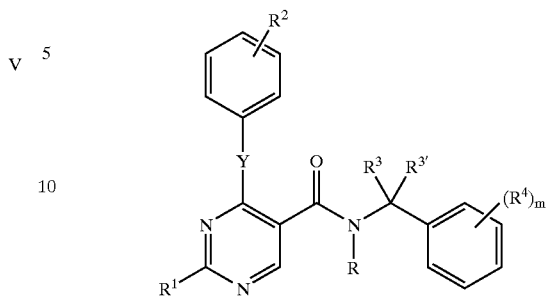

Ib wherein hal is Cl, Br or I, and Y, R¹, R², R³, R³', R⁴, R (for the purposes of these reaction schemes, the designation "R" includes R, $R^a$, $R^b$, $R^c$, $R^d$, $R^e$, $R^f$) and m have the significances given above, or reacting a compound of formula

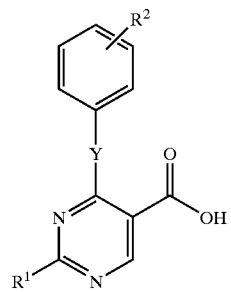

VIII with a compound of formula

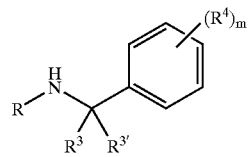

V to a compound of formula

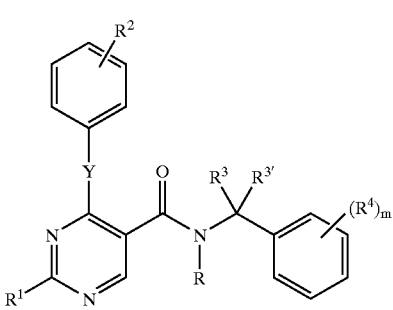

Ib wherein Y, R¹, R², R³, R³', R⁴, R (for the purposes of these reaction schemes, the designation "R" includes R, $R^a$, b,$R^c$, $R^d$, $R^e$, $R^f$) and m have the significances given above, or alkylating a compound of formula

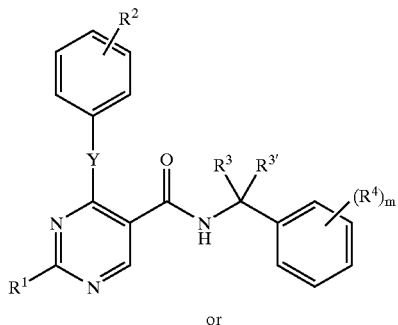

Ib1 or

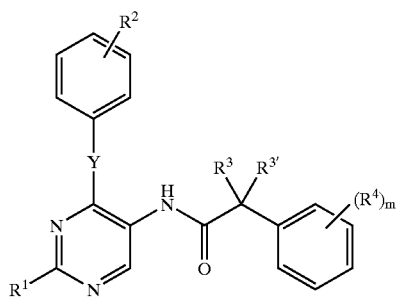

Ia1 to a compound of formula

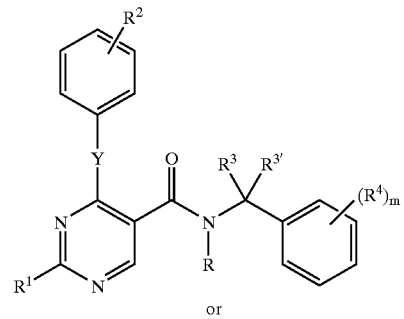

Ib or

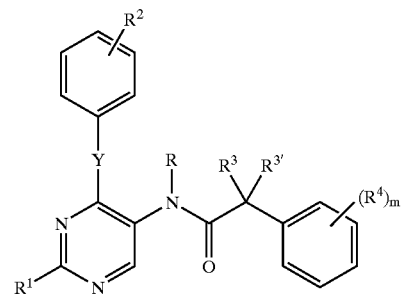

Ia wherein Y, $R^1$, $R^2$, $R^3$, $R^{3'}$, $R^4$, R (for the purposes of these reaction schemes, the designation "R" includes R, $R^a$, $R^b$, RC, $R^1$, $R^e$, $R^f$) and m have the significances given above, or transforming a compound of formula

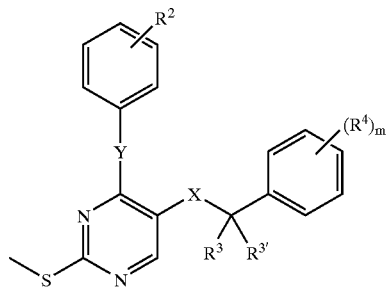

I-1 to a compound of formula

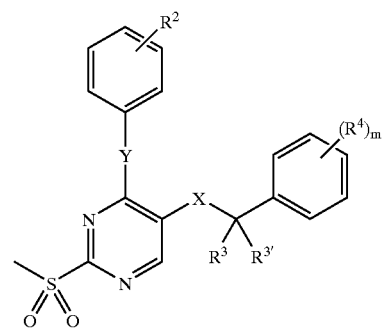

I-2 wherein X, Y, $R^1$, $R^2$, $R^3$, $R^{3'}$, $R^4$ and m have the significances given above, or reacting a compound of formula

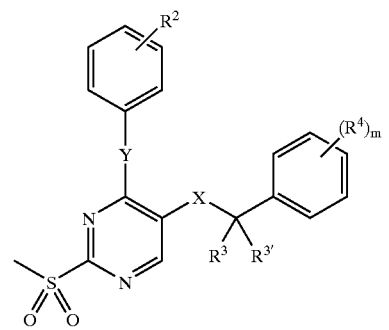

I-2 with a corresponding cyclic or non cyclic amine to a compound of formula

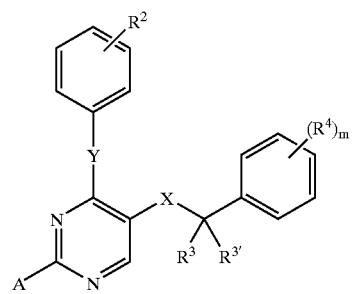

I-3 or with a corresponding alcohol to a compound of formula I-4

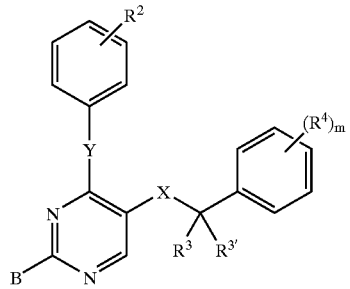

wherein Y, X, R$^1$, R$^2$, R$^3$, R$^{3'}$, R$^4$ and m have the significances given above, A is —N(R)—(CH$_2$)$_n$—N(R)$_2$, —N(R)$_2$ or a cyclic tertiary amine of the formula

and B is lower alkoxy, —O—(CH$_2$)$_n$—N(R)$_2$ or

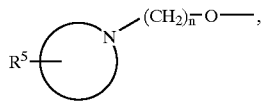

and R$^5$ is described as above, or modifying one or more substituents R$^1$, R$^2$, R$^3$, R$^{3'}$, R$^4$ or R (for the purposes of these reaction schemes, the designation "R" includes R, R$^a$, R$^b$, R$^c$, R$^d$, R$^e$, R$^f$) within the definitions given above, and if desired, converting the compound obtained into a pharmaceutically acceptable acid addition salt.

In accordance with process variant a) DIPEA (N-ethyldiisopropyl-amine) is added to a mixture of a compound of formula II and of a compound of formula III in dichloromethane and the mixture is stirred at temperatures between 25–40° C. The desired compound of formula Ia is isolated after purification in good yields.

Process variant b) describes the reaction of a compound of formula IV with a compound of formula V to a compound of formula Ib. The reaction is carried out in conventional manner, for example in a solvent like toluene in the presence of triethyl-amine. The mixture is refluxed for about 1 hour.

In accordance with process variant c) a compound of formula Ib is prepared. This reaction is carried out with DIPEA (N-ethyldiisopropyl-amine) which is added to a mixture of a compound of formula VI and of a compound of formula VII in dichloromethane.

A further method for the preparation of a compound of formula Ib is described in process variant d). A compound of formula VII is treated with a compound of formula V in the presence of EDCI (1-(3-dimethylaminopropyl)-3-ethyl-carbodiimide and HOBT (1-hydroxybenzotriazole hydrate) and triethylamine in conventional manner.

Compounds of formulas Ia or Ib may be prepared by alkylating the —NH-linking group with a corresponding lower alkyl iodine in the presence of NaH in DMF in accordance with process variant e) in conventional manner.

In accordance with process variant f) a compound of formula I-1 is treated with m-CPBA in dichloromethane to give a compound of formula I-2. Furthermore, this compound may then be treated with a corresponding cyclic amine, such as morpholine, piperazine or methyl-piperazine to a corresponding compound of formula I-3 or with a corresponding alcohol, such as 2-dimethylaminoethanol or N-(2-hydroxyethyl)morpholine, to a corresponding compound of formula I-4 in accordance with process variant g).

The salt formation is affected at room temperature in accordance with methods which are known per se and which are familiar to any person skilled in the art. Not only salts with inorganic acids, but also salts with organic acids come into consideration. Hydrochlorides, hydrobromides, sulphates, nitrates, citrates, acetates, maleates, succinates, methan-sulphonates, p-toluenesulphonates and the like are examples of such salts.

The following schemes 1–4 describe the processes for preparation of compounds of formula I in more detail. The starting materials are known compounds or may be prepared according to methods known in the art.

In the schemes the following abbreviations have been used:

| | |
|---|---|
| DIPEA | N-ethyldiisopropyl-amine |
| EDCI | 1-(3-dimethylaminopropyl)-3-ethyl-carbodiimide |
| HOBT | 1-hydroxybenzotriazole hydrate |
| DMF | dimethylformamid |
| m-CPBA | m-chloroperbenzoic acid |
| DPPA | diphenylphosphoryl azide |

Scheme 1

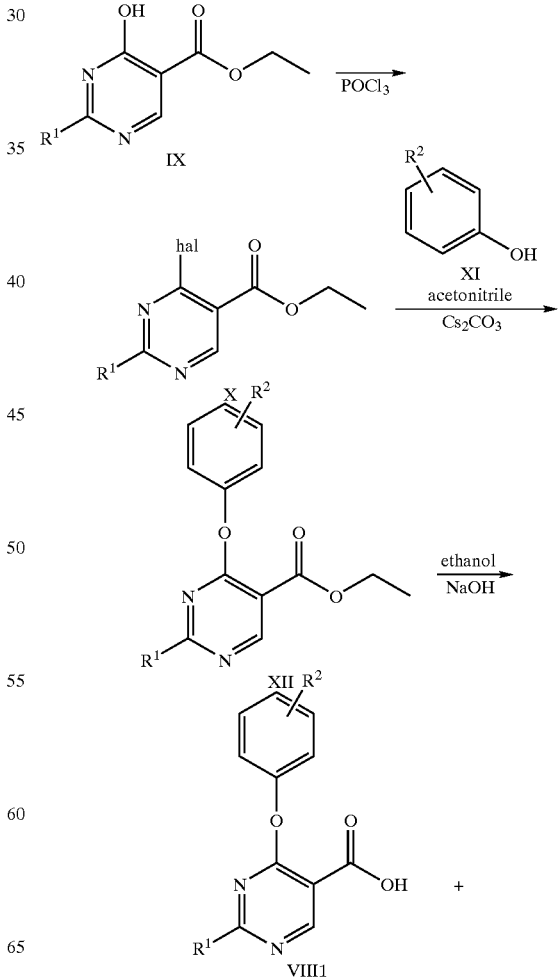

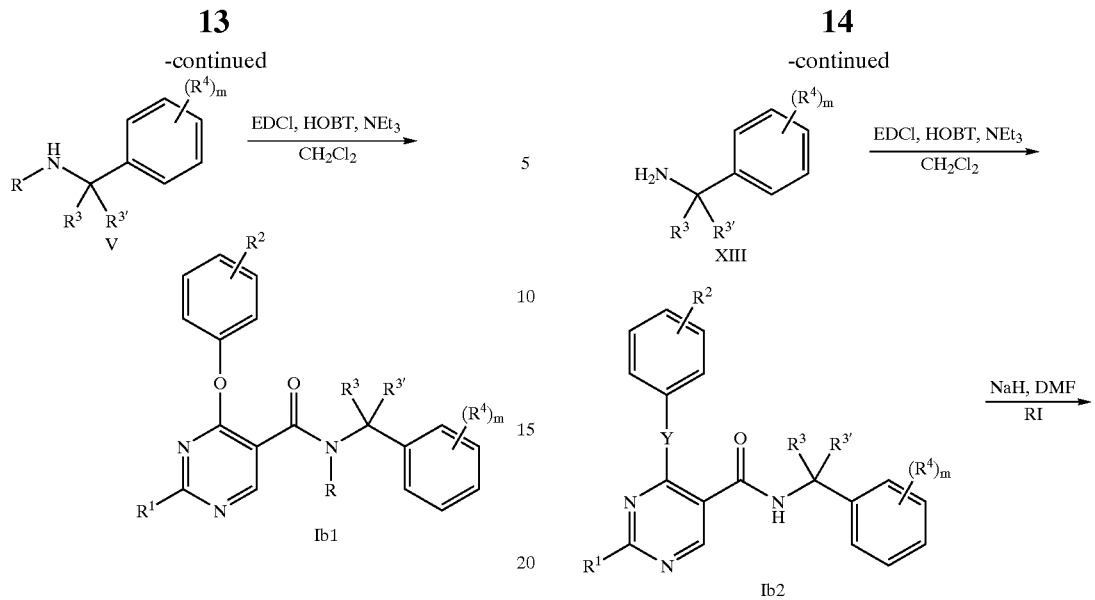

$R^1$, $R^2$, $R^3$, $R^{3'}$ and $R^4$ have the significances given above and R (for the purposes of these reaction schemes, the designation "R" includes R, $R^a$, $R^b$, $R^c$, $R^d$, $R^e$, $R^f$) is lower alkyl.

Scheme 2

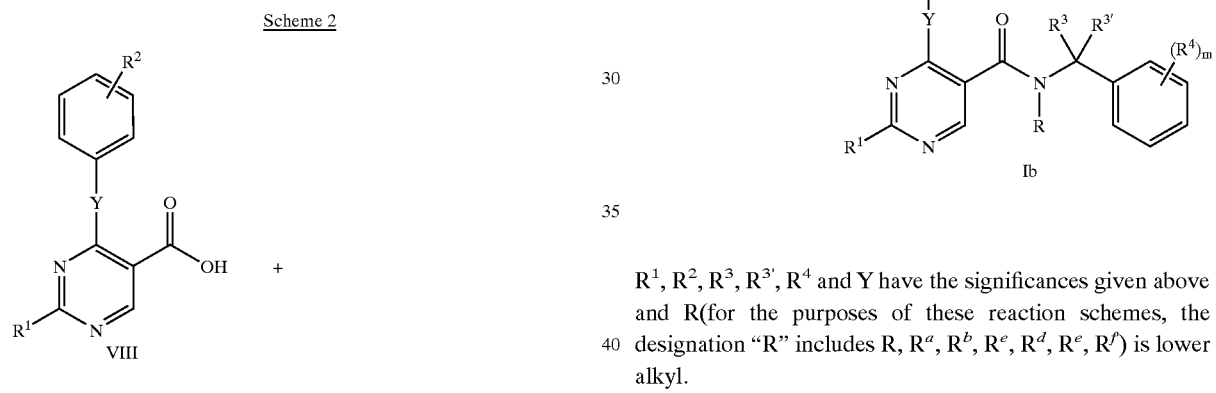

$R^1$, $R^2$, $R^3$, $R^{3'}$, $R^4$ and Y have the significances given above and R(for the purposes of these reaction schemes, the designation "R" includes R, $R^a$, $R^b$, $R^c$, $R^d$, $R^e$, $R^f$) is lower alkyl.

Scheme 3

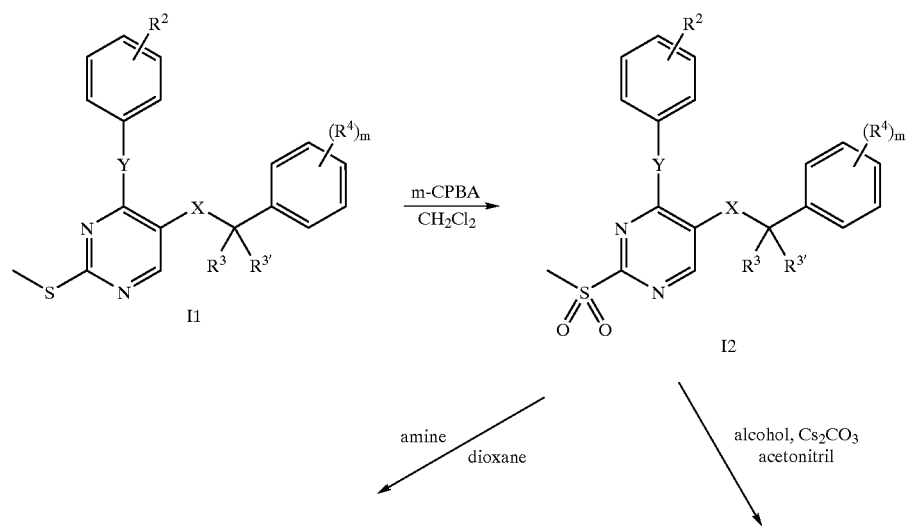

-continued

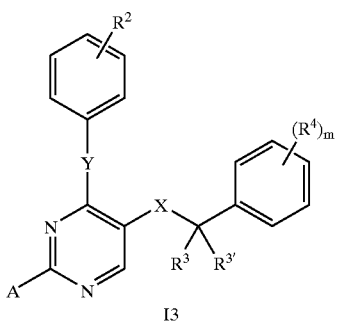
I3

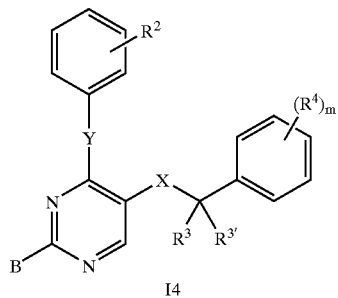
I4

$R^2$, $R^3$, $R^{3''}$, $R^4$, X,Y and m have the significances given above, A is —N(R)—(CH$_2$)$_n$—N(R)$_2$, —N(R)$_2$ or a cyclic tertiary amine of the formula

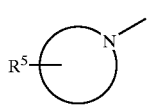

and B is lower alkoxy, —O—(CH$_2$)$_n$—N(R)$_2$ or

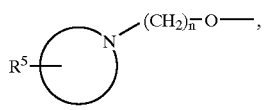

and $R^5$ is described as above.

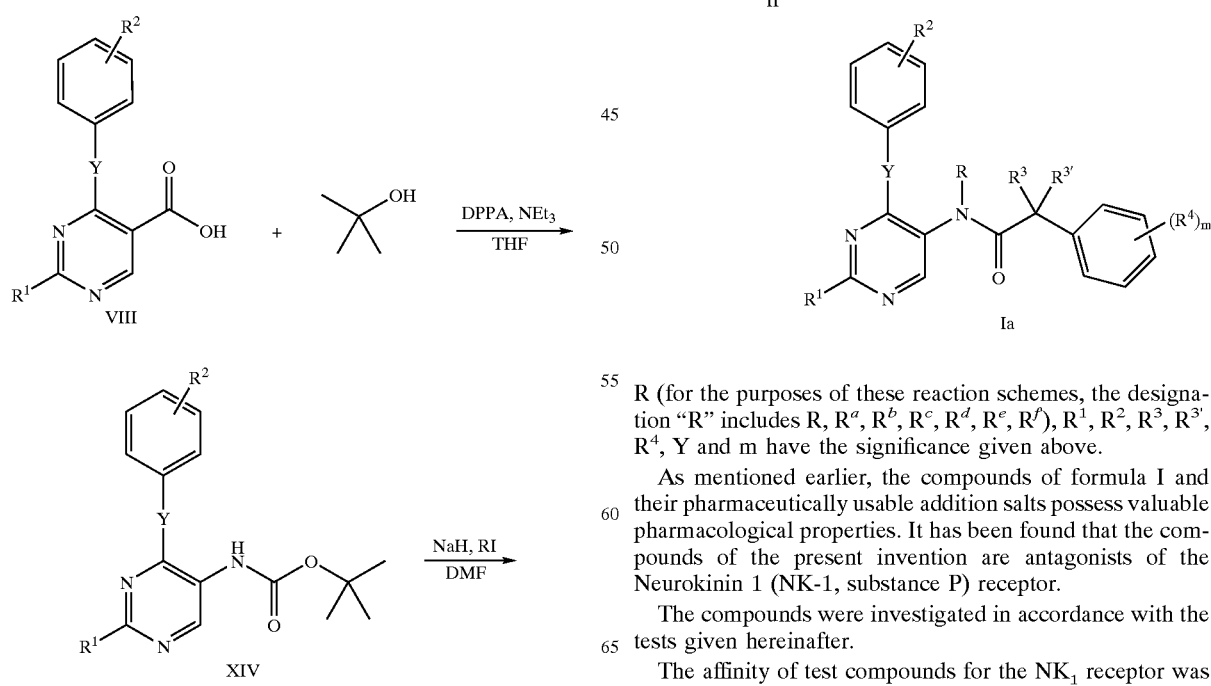

R (for the purposes of these reaction schemes, the designation "R" includes R, $R^a$, $R^b$, $R^c$, $R^d$, $R^e$, $R^f$), $R^1$, $R^2$, $R^3$, $R^{3'}$, $R^4$, Y and m have the significance given above.

As mentioned earlier, the compounds of formula I and their pharmaceutically usable addition salts possess valuable pharmacological properties. It has been found that the compounds of the present invention are antagonists of the Neurokinin 1 (NK-1, substance P) receptor.

The compounds were investigated in accordance with the tests given hereinafter.

The affinity of test compounds for the NK$_1$ receptor was evaluated at human NK$_1$ receptors in CHO cells infected with the human NK$_1$ receptor (using the Semliki virus expression system) and radiolabelled with [$^3$H]substance P (final concentration 0.6 nM). Binding assays were performed in HEPES buffer (50 mM, pH 7.4) containing BSA (0.04%) leupeptin (8 μg/ml), MnCl$_2$ (3 mM) and phosphoramidon (2 μM). Binding assays consisted of 250 μl of membrane suspension (1.25×10$^5$ cells/assay tube), 0.125 μl of displacing agent and 125 μl of [$^3$H]substance P. Displacement curves were determined with at least seven concentrations of the compound. The assay tubes were incubated for 60 min at room temperature after which time the tube contents were rapidly filtered under vacuum through GF/C filters presoaked for 60 min with PEI (0.3%) with 2×2 ml washes of HEPES buffer (50 mM, pH 7.4). The radioactivity retained on the filters was measured by scintillation counting. All assays were performed in triplicate in at least 2 separate experiments.

The affinity to the NK-1 receptor, given as pKi, is in the scope of 6.00–9.38 for the described compounds.

Examples of the pKi data for such compounds are described in the table below:

| Example No. | pKi |
|---|---|
| 1 | 7.38 |
| 4 | 8.54 |
| 7 | 8.33 |
| 11 | 6.77 |
| 15 | 7.55 |
| 19 | 6.71 |
| 23 | 7.01 |
| 29 | 6.50 |
| 39 | 7.79 |
| 44 | 7.70 |
| 49 | 9.04 |
| 52 | 9.10 |
| 63 | 8.02 |
| 73 | 7.49 |

The compounds of formula I as well as their pharmaceutically usable acid addition salts can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be affected rectally, e.g. in the form of suppositories, or parenterally, e.g. in the form of injection solutions.

The compounds of formula I and their pharmaceutically usable acid addition salts can be processed with pharmaceutically inert, inorganic or organic excipients for the production of tablets, coated tablets, dragees and hard gelatine capsules. Lactose, corn starch or derivatives thereof, talc, stearic acid or its salts etc can be used as such excipients e.g. for tablets, dragees and hard gelatine capsules.

Suitable excipients for soft gelatine capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, in the case of oral administration a daily dosage of about 10 to 1000 mg per person of a compound of formula I should be appropriate, although the above upper limit can also be exceeded when necessary.

The following Examples illustrate the present invention without limiting it. All temperatures are given in degrees Celsius.

EXAMPLE 1

2-Methylsulfanyl-4-o-tolyloxy-pyrimidine-5-carboxylic acid (3,5-bis-trifluoromethyl-benzyl)-methyl-amide a) 2-Methylsulfanyl-4-o-tolyloxy-pyrimidine-5-carboxylic acid ethyl ester To a solution of 5.40 g (23.31 mmol) 4-chloro-2-methylsulfanyl-pyrimidine-5-carboxylic acid ethyl ester in 150 ml acetonitrile 3.26 g (30.17 mmol) o-cresol and 30.25 g (92.83 mmol) Cs$_2$CO$_3$ were added and the reaction mixture was stirred for 14 h at RT. The suspension was poured into ice-water and extracted two times with CH$_2$Cl$_2$. The combined organic phases were dried (Na$_2$SO$_4$), filtered and evaporated to give 7.0 g (99%) 2-methylsulfanyl-4-o-tolyloxy-pyrimidine-5-carboxylic acid ethyl ester, which was directly used for the next step b) 2-Methansulfonyl-4-o-tolyloxy-pyrimidine-5-carboxylic acid To a solution of 7.0 g (23.0 mmol) 2-methylsulfanyl-4-o-tolyloxy-pyrimidine-5-carboxylic acid ethyl ester in 50 ml ethanol a solution of 1.37 g (34.50 mmol) sodiumhydroxide in 30 ml water was added and the resulting mixture was stirred 1 h at RT. The pH of the solution was adjusted to 1 with 25% HCl. The mixture was extracted twice with CH$_2$Cl$_2$. The combined organic phases were dried (Na$_2$SO$_4$), filtered and evaporated. The resulting solid was triturated twice with 10 ml diisopropylether, filtered off and dried to give 3.00 g (47%) 2-methylsulfanyl-4-o-tolyloxy-pyrimidine-5-carboxylic acid as a colorless solid, MS (ISN): 257.1 (M-H)$^-$.

c) 2-Methylsulfanyl-4-o-tolyloxy-pyrimidine-5-carboxylic acid (3,5-bis-trifluoromethyl-benzyl)-methyl-amide To a solution of 1.0 g (3.62 mmol) 2-methylsulfanyl-4-o-tolyloxy-pyrimidine-5-carboxylic acid in 60 ml CH$_2$Cl$_2$ 1.0 ml (7.24 mmol) triethylamine, 0.554 g (3.62 mmol) 1-hydroxy-benzotriazole and 0.69 g (3.62 mmol) N-(3-dimethylaminopropyl)-N'-ethylcarbodiimide hydrochloride 1.11 g (4.34 mmol) (3,5-bis-trifluormethyl-benzyl)-methyl-amide were added. The reaction mixture was stirred for 16 hrs. The reaction mixture was diluted with 20 ml CH$_2$Cl$_2$, washed with 50 ml 0.5N HCl and 50 ml H$_2$O. The aqueous layers were backextracted with 50 ml CH$_2$Cl$_2$. The combined organic layers were dried (MgSO$_4$), filtered and evaporated. The residue was purified by chromatography (SiO$_2$, CH$_2$Cl$_2$/MeOH 40:1) to give 1.80 g (96%) 2-methylsulfanyl-4-o-tolyloxy-pyrimidine-5-carboxylic acid (3,5-bis-trifluoromethyl-benzyl)-methyl-amide as a colorless foam, MS (EI): 515 (M$^+$).

EXAMPLE 2

2-Methanesulfonyl-4-o-tolyloxy-pyrimidine-5-carboxylic acid (3,5-bis-trifluoromethyl-benzyl)-methyl-amide To a solution of 1.70 g (3.30 mmol) 2-methylsulfanyl-4-o-tolyloxy-pyrimidine-5-carboxylic acid (3,5-bistrifluoromethyl-benzyl)-methyl-amide in 70 ml $CH_2Cl_2$ 2.03 g (8.24 mmol) 3-chloroperbenzoic acid (70%) was added at 5° and the reaction mixture stirred for 2 hrs. at RT. After addition of 150 ml sat. $NaHCO_3$-solution, the layers were separated, the organic phase washed with sat. $NaHCO_3$-solution, dried ($Na_2SO_4$), filtered and evaporated. The residue was purified by chromatography ($SiO_2$, $CH_2Cl_2$/ethyl acetate 9:1) to give 1.50 g (83%) 2-methanesulfonyl-4-o-tolyloxy-pyrimidine-5-carboxylic acid (3,5-bis-trifluoromethyl-benzyl)-methyl-amide as a colorless solid, MS (ISP): 548.1 $(M+H)^+$.

EXAMPLE 3

2-Morpholin-4-yl-4-o-tolyloxy-pyrimidine-5-carboxylic acid (3,5-bis-trifluoromethyl-benzyl)-methyl-amide To a solution of 0.2 g (0.37 mmol) 2-methanesulfonyl-4-o-tolyloxy-pyrimidine-5-carboxylic acid (3,5-bis-trifluoromethyl-benzyl)-methyl-amide in 10 ml dioxane 0.08 ml (0.91 mmol) morpholine was added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/MeOH 40:1) to give 0.18 g (88%) 2-morpholin-4-yl-4-o-tolyloxy-pyrimidine-5-carboxylic acid (3,5-bis-trifluoromethyl-benzyl)-methyl-amide as a colorless oil, MS (ISP): 555.2 $(M+H)^+$.

EXAMPLE 4

2-(4-Methyl-piperazin-1-yl)-4-o-tolyloxy-pyrimidine-5-carboxylic acid (3,5-bis-trifluoromethyl-benzyl)-methyl-amide To a solution of 0.25 g (0.46 mmol) 2-methanesulfonyl-4-o-tolyloxy-pyrimidine-5-carboxylic acid (3,5-bis-trifluoromethyl-benzyl)-methyl-amide in 10 ml dioxane 0.12 ml (1.14 mmol) 1-methylpiperazine was added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/MeOH/NH4OH 140:10:1) to give 0.2 g (77%) 2-(4-methyl-piperazin-1-yl)-4-o-tolyloxy-pyrimidine-5-carboxylic acid (3,5-bis-trifluoromethyl-benzyl)-methyl-amide as a colorless foam, MS (ISP): 563.3 $(M+H)^+$.

EXAMPLE 5

2-Piperazin-1-yl-4-o-tolyloxy-pyrimidine-5-carboxylic acid (3,5-bis-trifluoromethyl-benzyl)-methyl-amide To a solution of 0.32 g (0.58 mmol) 2-methanesulfonyl-4-o-tolyloxy-pyrimidine-5-carboxylic acid (3,5-bis-trifluoromethyl-benzyl)-methyl-amide in 10 ml dioxane 0.125 g (1.46 mmol) piperazine was added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, CH2Cl2/MeOH/$NH_4OH$ 110:10:1) to give 0.25 g (77%) 2-piperazin-1-yl-4-o-tolyloxy-pyrimidine-5-carboxylic acid (3,5-bis-trifluoromethyl-benzyl)-methyl-amide as a colorless foam, MS (ISP): 554.2 $(M+H)^+$.

EXAMPLE 6

2-(2-Dimethylamino-ethylamino)-4-o-tolyloxy-pyrimidine-5-carboxylic acid (3,5-bis-trifluoromethyl-benzyl)-methyl-amide To a solution of 0.25 g (0.46 mmol) 2-methanesulfonyl-4-o-tolyloxy-pyrimidine-5-carboxylic acid (3,5-bis-trifluoromethyl-benzyl)-methyl-amide in 10 ml dioxane 0.125 ml (1.14 mmol) 2-dimethylaminoethyl amine was added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/MeOH/NH4OH 140:10:1) to give 0.15 g (59%) 2-(2-dimethylamino-ethylamino)-4-o-tolyloxy-pyrimidine-5-carboxylic acid (3,5-bis-trifluoromethyl-benzyl)-methyl-amide as a colorless foam, MS (SP): 556.2 $(M+H)^+$.

EXAMPLE 7

2-(2-Morpholin-4-yl-ethoxy)-4-o-tolyloxy-pyrimidine-5-carboxylic acid (3,5-bis-trifluoromethyl-benzyl)-methyl-amide To a solution of 0.2 g (0.37 mmol) 2-methanesulfonyl-4-o-tolyloxy-pyrimidine-5-carboxylic acid (3,5-bis-trifluoromethyl-benzyl)-methyl-amide in 10 ml acetonitrile 0.066 ml (0.55 mmol) N-(2-hydroxyethyl)morpholine and 0.595 g (1.83 mmol) $Cs_2CO_3$ were added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/MeOH/$NH_4OH$ 140:10:1) to give 0.12 g (54%) 2-(2-morpholin-4-yl-ethoxy)-4-o-tolyloxy-pyrimidine-5-carboxylic acid (3,5-bis-trifluoromethyl-benzyl)-methyl-amide as a colorless foam, MS (ISP): 599.1 $(M+H)^+$.

EXAMPLE 8

2-(2-Dimethylamino-ethoxy)-4-o-tolyloxy-pyrimidine-5-carboxylic acid (3,5-bis-trifluoromethyl-benzyl)-methyl-amide To a solution of 0.25 g (0.46 mmol) 2-methanesulfonyl-4-o-tolyloxy-pyrimidine-5-carboxylic acid (3,5-bis-trifluoromethyl-benzyl)-methyl-amide in 10 ml acetonitrile 0.069 ml (0.68 mmol) 2-dimethylaminoethanol and 0.743 g (2.28 mmol) $Cs_2CO_3$ were added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/MeOH/$NH_4OH$ 140:10:1) to give 0.15 g (59%) 2-(2-dimethylamino-ethoxy)-4-o-tolyloxy-pyrimidine-5-carboxylic acid (3,5-bis-trifluoromethyl-benzyl)-methyl-amide as a light yellow oil, MS (ISP): 557.3 $(M+H)^+$.

EXAMPLE 9

2-Methylsulfanyl-4-o-tolyloxy-pyrimidine-5-carboxylic acid (3,5-dimethoxy-benzyl)-methyl-amide In an analogous manner to that described in Example 1c) there was obtained from 2-methylsulfanyl-4-o-tolyloxypyrimidine-5-carboxylic acid and (3,5-dimethoxy-benzyl)-methyl-amine 2-methylsulfanyl-4-o-tolyloxy-pyrimidine-5-carboxylic acid (3,5-dimethoxy-benzyl)-methyl-amide as a colorless oil, MS (EI): 439.1 (M+).

EXAMPLE 10

2-Methanesulfonyl-4-o-tolyloxy-pyrimidine-5-carboxylic acid (3,5-dimethoxy-benzyl)-methyl-amide In an analogous manner to that described in Example 2 there was obtained from 2-methylsulfanyl-4-o-tolyloxy-pyrimidine-5-carboxylic acid (3,5-dimethoxy-benzyl)-methyl-amide and 3-chloroperbenzoic acid 2-methanesulfonyl-4-o-tolyloxy-pyrimidine-5-carboxylic acid (3,5-dimethoxy-benzyl)-methyl-amide as a colorless foam, MS (ISP): 472.1 (M+H)+.

EXAMPLE 11

2-(4-Methyl-piperazin-1-yl)-4-o-tolyloxy-pyrimidine-5-carboxylic acid (3,5-dimethoxy-benzyl)-methyl-amide In analogous manner to that described in Example 4 there was obtained from 2-methanesulfonyl-4-o-tolyloxy-pyrimidine-5-carboxylic acid (3,5-dimethoxy-benzyl)-methyl-amide and 1-methylpiperazine 2-(4-methyl-piperazin-1-yl)-4-o-tolyloxy-pyrimidine-5-carboxylic acid (3,5-dimethoxy-benzyl)-methyl-amide as a colorless foam, MS (ISP): 492.3 (M+H)+.

EXAMPLE 12

2-(2-Dimethylamino-ethoxy)-4-o-tolyloxy-pyrimidine-5-carboxylic acid (3,5-dimethoxy-benzyl)-methyl-amide In analogous manner to that described in Example 8 there was obtained from 2-methanesulfonyl-4-o-tolyloxy-pyrimidine-5-carboxylic acid (3,5-dimethoxy-benzyl)-methyl-amide and 2-dimethylaminoethanol 2-(2-dimethylamino-ethoxy)-4-o-tolyloxy-pyrimidine-5-carboxylic acid (3,5-dimethoxy-benzyl)-methyl-amide as a colorless oil, MS (ISP): 481.4 (M+H)+.

EXAMPLE 13

2-Methylsulfanyl-4-o-tolyloxy-pyrimidine-5-carboxylic acid (3,5-dimethyl-benzyl)-methyl-amide In an analogous manner to that described in Example 1c there was obtained from 2-methylsulfanyl-4-o-tolyloxy-pyrimidine-5-carboxylic acid and (3,5-dimethyl-benzyl)-methyl-amine 2-methylsulfanyl-4-o-tolyloxy-pyrimidine-5-carboxylic acid (3,5-dimethyl-benzyl)-methyl-amide as a colorless oil, MS (ISP): 408.3 (M+H)+.

EXAMPLE 14

2-Methanesulfonyl-4-o-tolyloxy-pyrimidine-5-carboxylic acid (3,5-dimethyl-benzyl)-methyl-amide In an analogous manner to that described in Example 2 there was obtained from 2-methylsulfanyl-4-o-tolyloxy-pyrimidine-5-carboxylic acid (3,5-dimethyl-benzyl)-methyl-amide and 3-chloroperbenzoic acid 2-methanesulfonyl-4-o-tolyloxy-pyrimidine-5-carboxylic acid (3,5-dimethyl-benzyl)-methyl-amide as a colorless foam, MS (ISP): 440.4 (M+H)+.

EXAMPLE 15

2-(4-Methyl-piperazin-1-yl)-4-o-tolyloxy-pyrimidine-5-carboxylic acid (3,5-dimethyl-benzyl)-methyl-amide In an analogous manner to that described in Example 4 there was obtained from 2-methanesulfonyl-4-o-tolyloxy-pyrimidine-5-carboxylic acid (3,5-dimethyl-benzyl)-methyl-amide and 1-methylpiperazine 2-(4-methyl-piperazin-1-yl)-4-o-tolyloxy-pyrimidine-5-carboxylic acid (3,5-dimethyl-benzyl)-methyl-amide as a white foam, MS (ISP): 460.5 (M+H)+.

EXAMPLE 16

2-(2-Dimethylamino-ethoxy)-4-o-tolyloxy-pyrimidine-5-carboxylic acid (3,5-dimethyl-benzyl)-methyl-amide In an analogous manner to that described in Example 8 there was obtained from 2-methanesulfonyl-4-o-tolyloxy-pyrimidine-5-carboxylic acid (3,5-dimethyl-benzyl)-methyl-amide and 2-dimethylaminoethanol 2-(2-dimethylamino-ethoxy)-4-o-tolyloxy-pyrimidine-5-carboxylic acid (3,5-dimethyl-benzyl)-methyl-amide as a colorless oil, MS (ISP): 449.5 (M+H)+.

EXAMPLE 17

2-Methylsulfanyl-4-o-tolyloxy-pyrimidine-5-carboxylic acid 3,5-dichloro-benzylamide In an analogous manner to that described in Example 1c) there was obtained from 2-methylsulfanyl-4-o-tolyloxy-pyrimidine-5-carboxylic acid and 3,5-dichlorobenzylamine 2-methylsulfanyl-4-o-tolyloxy-pyrimidine-5-carboxylic acid 3,5-dichloro-benzylamide as a light yellow oil, MS (EI): 433 (M+).

EXAMPLE 18

2-Methanesulfonyl-4-o-tolyloxy-pyrimidine-5-carboxylic acid 3,5-dichloro-benzylamide In an analogous manner to that described in Example 2 there was obtained from 2-methylsulfanyl-4-o-tolyloxy-pyrimidine-5-carboxylic acid 3,5-dichloro-benzylamide and 3-chloroperbenzoic acid 2-methanesulfonyl-4-o-tolyloxy-pyrimidine-5-carboxylic acid 3,5-dichloro-benzylamide as a colorless solid, MS (ISP): 466.2 (M+H)+.

EXAMPLE 19

2-(4-Methyl-piperazin-1-yl)-4-o-tolyloxy-pyrimidine-5-carboxylic acid 3,5-dichloro-benzylamide In an analogous manner to that described in Example 4 there was obtained from 2-methanesulfonyl-4-o-tolyloxy-pyrimidine-5-carboxylic acid 3,5-dichloro-benzylamide and 1-methylpiperazine 2-(4-methyl-piperazin-1-yl)-4-o-tolyloxy-pyrimidine-5-carboxylic acid 3,5-dichloro-benzylamide as a colorless solid, MS (ISP): 486.3 (M+H)+.

EXAMPLE 20

2-Methylsulfanyl-4-o-tolyloxy-pyrimidine-5-carboxylic acid (3,5-dichloro-benzyl)-methyl-amide To a solution of 0.6 g (1.8 mmol) 2-methylsulfanyl-4-o-tolyloxy-pyrimidine-5-carboxylic acid 3,5-dichlorobenzylamide in 20 ml N,N-dimethylformamide 0.096 g (2.4 mmol) sodiumhydride (60% dispersion in mineraloil) was added and the mixture stirred for 1 h. After the addition of 0.18 ml (2.9 mmol) methyl iodide at 0°, the reaction mixture was stirred for 3 hrs. at RT. The reaction mixture was distributed between 50 ml H$_2$O, 50 ml brine and 50 ml CH$_2$Cl$_2$. The phases were separated, and the aqueous layer extracted twice with 50 ml CH$_2$Cl$_2$. The combined organic layers were dried (MgSO$_4$), filtered and evaporated. The residue was purified by chromatography (SiO$_2$, CH$_2$Cl$_2$/ethyl acetate 19:1) to give 0.5 g (61%) 2-methylsulfanyl-4-o-tolyloxy-pyrimidine-5-carboxylic acid (3,5-dichloro-benzyl)-methyl-amide as a light yellow oil, MS (EI): 447.1 (M$^+$).

EXAMPLE 21

2-Methanesulfonyl-4-o-tolyloxy-pyrimidine-5-carboxylic acid (3,5-dichloro-benzyl)-methyl-amide In an analogous manner to that described in Example 2 there was obtained from 2-methylsulfanyl-4-o-tolyloxy-pyrimidine-5-carboxylic acid (3,5-dichloro-benzyl)-methyl-amide and 3-chloroperbenzoic acid 2-methanesulfonyl-4-o-tolyloxy-pyrimidine-5-carboxylic acid (3,5-dichloro-benzyl)-methyl-amide as a colorless foam, MS (ISP): 480.2 (M+H)$^+$.

EXAMPLE 22

2-(4-Methyl-piperazin-1-yl)-4-o-tolyloxy-pyrimidine-5-carboxylic acid (3,5-dichloro-benzyl)-methyl-amide In an analogous manner to that described in Example 4 there was obtained from 2-methanesulfonyl-4-o-tolyloxy-pyrimidine-5-carboxylic acid (3,5-dichloro-benzyl)-methyl-amide and 1-methylpiperazine 2-(4-methyl-piperazin-1-yl)-4-o-tolyloxy-pyrimidine-5-carboxylic acid (3,5-dichloro-benzyl)-methyl-amide as a colorless foam, MS (ISP): 500.2 (M+H)$^+$.

EXAMPLE 23

2-Methylsulfanyl-4-phenoxy-pyrimidine-5-carboxylic acid (3,5-bis-trifluoromethyl-benzyl)-methyl-amide In an analogous manner to that described in Example 1a) there was obtained from 4-chloro-2-methylsulfanyl-pyrimidine-5-carboxylic acid ethyl ester and phenol 2-methylsulfanyl-4-phenoxy-pyrimidine-5-carboxylic acid ethyl ester, which was saponified as described in Example 1b) and reacted with (3,5-bis-trifluormethyl-benzyl)-methyl-amine to give as described in Example 1c) 2-methylsulfanyl-4-phenoxy-pyrimidine-5-carboxylic acid (3,5-bis-trifluoromethyl-benzyl)-methyl-amide as a colorless solid, MS (TSP): 501 (M$^+$).

EXAMPLE 24

2-Methanesulfonyl-4-phenoxy-pyrimidine-5-carboxylic acid (3,5-bis-trifluoromethyl-benzyl)-methyl-amide In an analogous manner to that described in Example 2 there was obtained from 2-methylsulfanyl-4-phenoxy-pyrimidine-5-carboxylic acid (3,5-bis-trifluoromethyl-benzyl)-methyl-amide and 3-chloroperbenzoic acid 2-methanesulfonyl-4-phenoxy-pyrimidine-5-carboxylic acid (3,5-bis-trifluoromethyl-benzyl)-methyl-amide as a colorless solid, MS (TSP): 533 (M$^+$).

EXAMPLE 25

2-(4-Methyl-piperazin-1-yl)-4-phenoxy-pyrimidine-5-carboxylic acid (3,5-bis-trifluoromethyl-benzyl)-methyl-amide In an analogous manner to that described in Example 4 there was obtained from 2-methanesulfonyl-4-phenoxy-pyrimidine-5-carboxylic acid (3,5-bis-trifluoromethyl-benzyl)-methyl-amide and 1-methylpiperazine 2-(4-methyl-piperazin-1-yl)-4-phenoxy-pyrimidine-5-carboxylic acid (3,5-bis-trifluoromethyl-benzyl)-methyl-amide as a colorless solid, MS (ISP): 554.2 (M+H)$^+$.

EXAMPLE 26

4-(2—Chloro-phenoxy)-2-(4-methyl-piperazin-1-yl)-pyrimidine-5-carboxylic acid (3,5-bis-trifluoromethyl-benzyl)-methyl-amide In an analogous manner to that described in Example 1a) there was obtained from 4-chloro-2-methylsulfanyl-pyrimidine-5-carboxylic acid ethyl ester and 2-chloro phenol 4-(2-chloro-phenoxy)-2-methylsulfanyl-pyrimidine-5-carboxylic acid ethyl ester which was saponified as described in Example 1b) and reacted with (3,5-bis-trifluormethyl-benzyl)-methyl-amine to give as described in Example 1c) 4-(2-chloro-phenoxy)-2-(4-methyl-piperazin-1-yl)-pyrimidine-5-carboxylic acid (3,5-bis-trifluoromethyl-benzyl)-methyl-amide as a colorless solid, MS (ISP): 536.2 (M+H)$^+$.

EXAMPLE 27

4-(2—Chloro-phenoxy)-2-methanesulfonyl-pyrimidine-5-carboxylic acid (3,5-bis-trifluoromethyl-benzyl)-methyl-amide In an analogous manner to that described in Example 2 there was obtained from 4-(2-chloro-phenoxy)-2-(4-methyl-piperazin-1-yl)-pyrimidine-5-carboxylic acid (3,5-bis-trifluoromethyl-benzyl)-methyl-amide and 3-chloroperbenzoic acid 4-(2-chloro-phenoxy)-2-methanesulfonyl-pyrimidine-5-carboxylic acid (3,5-bis-trifluoromethyl-benzyl)-methyl-amide as a colorless solid, MS (ISP): 560.0 (M+H)$^+$.

EXAMPLE 28

4-(2—Chloro-phenoxy)-2-(4-methyl-piperazin-1-yl)-pyrimidine-5-carboxylic acid (3,5-bis-trifluoromethyl-benzyl)-methyl-amide In an analogous manner to that described in Example 4 there was obtained from 4-(2-chloro-phenoxy)-2-methanesulfonyl-pyrimidine-5-carboxylic acid (3,5-bis-trifluoromethyl-benzyl)-methyl-amide and 1-methylpiperazine 4-(2-chloro-phenoxy)-2-(4-methyl-piperazin-1-yl)-pyrimidine-5-carboxylic acid (3,5-bis-trifluoromethyl-benzyl)-methyl-amide as a colorless solid, MS (ISP): 588.2 (M+H)$^+$.

EXAMPLE 29

4-(2-Methoxy-phenoxy)-2-(4-methyl-piperazin-1-yl)-pyrimidine-5-carboxylic acid (3,5-bis-trifluoromethyl-benzyl)-methyl-amide In an analogous manner to that described in Example 1a) there was obtained from 4-chloro-2-methylsulfanylpyrimidine-5-carboxylic acid ethyl ester and 2-methoxyphenol 4-(2-methoxy-phenoxy)-2-methylsulfanyl-pyrimidine-5-carboxylic acid ethyl ester which was saponified as described in Example 1b) and reacted with (3,5-bis-trifluormethyl-benzyl)-methyl-amine to give as described in Example 1c) 4-(2-methoxy-phenoxy)-2-(4-methyl-piperazin-1-yl)-pyrimidine-5-carboxylic acid (3,5-bis-trifluoromethyl-benzyl)-methyl-amide as a colorless solid, MS (ISP): 532.1 $(M+H)^+$.

EXAMPLE 30

4-(2-Methoxy-phenoxy)-2-methanesulfonyl-pyrimidine-5-carboxylic acid (3,5-bis-trifluoromethyl-benzyl)-methyl-amide In an analogous manner to that described in Example 2 there was obtained from 4-(2-methoxy-phenoxy)-2-(4-methyl-piperazin-1-yl)-pyrimidine-5-carboxylic acid (3,5-bis-trifluoromethyl-benzyl)-methyl-amide and 3-chloroperbenzoic acid 4-(2-methoxy-phenoxy)-2-methanesulfonyl-pyrimidine-5-carboxylic acid (3,5-bis-trifluoromethyl-benzyl)-methyl-amide as a colorless solid, MS (ISP): 564.2 $(M+H)^+$.

EXAMPLE 31

4-(2-Methoxy-phenoxy)-2-(4-methyl-piperazin-1-yl)-pyrimidine-5-carboxylic acid (3,5-bis-trifluoromethyl-benzyl)-methyl-amide In an analogous manner to that described in Example 4 there was obtained from 4-(2-methoxy-phenoxy)-2-methanesulfonyl-pyrimidine-5-carboxylic acid (3,5-bis-trifluoromethyl-benzyl)-methyl-amide and 1-methylpiperazine 4-(2-methoxy-phenoxy)-2-(4-methyl-piperazin-1-yl)-pyrimidine-5-carboxylic acid (3,5-bis-trifluoromethyl-benzyl)-methyl-amide as a colorless solid, MS (ISP): 584.1 $(M+H)^+$.

EXAMPLE 32

2-(2-Dimethylamino-ethylamino)-4-(2-methoxy-phenoxy)-pyrimidine-5-carboxylic acid (3,5-bis-trifluoromethyl-benzyl)-methyl-amide In an analogous manner to that described in Example 6 there was obtained from 4-(2-methoxy-phenoxy)-2-methanesulfonyl-pyrimidine-5-carboxylic acid (3,5-bis-trifluoromethyl-benzyl)-methyl-amide and 2-dimethylaminoethyl amine 2-(2-dimethylamino-ethylamino)-4-(2-methoxy-phenoxy)-pyrimidine-5-carboxylic (3,5-bis-trifluoromethyl-benzyl)-methyl-amide as a colorless solid, MS (ISP): 572.1 $(M+H)^+$.

EXAMPLE 33

4-(2-Fluor-phenoxy)-2-methansulfonyl-pyrimidine-5-carboxylic acid (3,5-bis-trifluoromethyl-benzyl)-methyl-amide In an analogous manner to that described in Example 1a) there was obtained from 4-chloro-2-methylsulfanyl-pyrimidine-5-carboxylic acid ethyl ester and 4-fluoro-phenol 4-(4-fluoro-phenoxy)-2-methylsulfanyl-pyrimidine-5-carboxylic acid ethyl ester which was saponified as described in Example 1b) and reacted with (3,5-bis-trifluormethyl-benzyl)-methyl-amine to give as described in Example 1c) 4-(4-fluoro-phenoxy)-2-methansulfonyl-pyrimidine-5-carboxylic acid (3,5-bis-trifluoromethyl-benzyl)-methyl-amide as a colorless solid, MS (SP): 520.1 $(M+H^+)$.

EXAMPLE 34

4-(4-Fluoro-phenoxy)-2-methanesulfonyl-pyrimidine-5-carboxylic acid (3,5-bis-trifluoromethyl-benzyl)-methyl-amide In an analogous manner to that described in Example 2 there was obtained from 4-(4-fluoro-phenoxy)-2-methansulfonyl-pyrimidine-5-carboxylic acid (3,5-bis-trifluoromethyl-benzyl)-methyl-amide and 3-chloroperbenzoic acid 4-(4-fluoro-phenoxy)-2-methanesulfonyl-pyrimidine-5-carboxylic acid (3,5-bis-trifluoromethyl-benzyl)-methyl-amide as a colorless solid, MS (ISP): 552.0 $(M+H)^+$.

EXAMPLE 35

4-(4-Fluoro-phenoxy)-2-(4-methyl-piperazin-1-yl)-pyrimidine-5-carboxylic acid (3,5-bis-trifluoromethyl-benzyl)-methyl-amide In an analogous manner to that described in Example 4 there was obtained from 4-(4-fluoro-phenoxy)-2-methanesulfonyl-pyrimidine-5-carboxylic acid (3,5-bis-trifluoromethyl-benzyl)-methyl-amide and 1-methylpiperazine 4-(4-fluoro-phenoxy)-2-(4-methyl-piperazin-1-yl)-pyrimidine-5-carboxylic acid (3,5-bis-trifluoromethyl-benzyl)-methyl-amide as a white foam, MS (EI): 571 $(M^+)$.

EXAMPLE 36

4-(4-Fluoro-phenoxy)-2-piperazin-1-yl-pyrimidine-5-carboxylic acid (3,5-bis-trifluoromethyl-benzyl)-methyl-amide In an analogous manner to that described in Example 5 there was obtained from 4-(4-fluoro-phenoxy)-2-methanesulfonyl-pyrimidine-5-carboxylic acid (3,5-bis-trifluoromethyl-benzyl)-methyl-amide and piperazine 4-(4-fluoro-phenoxy)-2-piperazin-1-yl-pyrimidine-5-carboxylic acid (3,5-bis-trifluoromethyl-benzyl)-methyl-amide as a colorless foam, MS (ISP): 558.2 $(M+H)^+$.

EXAMPLE 37

2-(2-Dimethylamino-ethylamino)-4-(4-fluoro-phenoxy)-pyrimidine-5-carboxylic acid (3,5-bis-trifluoromethyl-benzyl)-methyl-amide In an analogous manner to that described in Example 6 there was obtained from 4-(4-fluoro-phenoxy)-2-methanesulfonyl-pyrimidine-5-carboxylic acid (3,5-bis-trifluoromethyl-benzyl)-methyl-amide and dimethylaminoethyl amine 2-(2-dimethylamino-ethylamino)-4-(4-fluoro-phenoxy)-pyrimidine-5-carboxylic acid (3,5-bis-trifluoromethyl-benzyl)-methyl-amide as a colorless foam, MS (ISP): 560.2 $(M+H)^+$.

EXAMPLE 38

2-(2-Dimethylamino-ethoxy)-4-(4-fluoro-phenoxy)-pyrimidine-5-carboxylic acid (3,5-bis-trifluoromethyl-benzyl)-methyl-amide In an analogous manner to that described in Example 8 there was obtained from 4-(4-fluoro-phenoxy)-2-methanesulfonyl-pyrimidine-5-carboxylic acid (3,5-bis-trifluoromethyl-benzyl)-methyl-amide and 2-dimethylaminoethanol 2-(2-dimethylamino-ethoxy)-4-(4- fluoro-phenoxy)-pyrimidine-5-carboxylic acid (3,5-bis-trifluoromethyl-benzyl)-methyl-amide as a colorless foam, MS (ISP): 561.3 (M+H)$^+$.

EXAMPLE 39

2-Pyridin-4-yl-4-o-tolyloxy-pyrimidine-5-carboxylic acid (3,5-bis-trifluoromethyl-benzyl)-methyl-amide a) 4—Chloro-2-pyridin-4-yl-pyrimidine-5-carboxylic acid ethyl ester A suspension of 4.78 g (19.5 mmol) 4-hydroxy-2-pyridin-4-yl-pyrimidine-5-carboxylic acid ethyl ester in 20 ml POCl$_3$ was heated at reflux for 1 h. The solution was cooled to RT and poured into 100 ml ice-water. The pH of the solution was adjusted to 8 with sat.NaHCO$_3$-solution. The water-phase was extracted three times with 80 ml CH$_2$Cl$_2$. The combined organic phases were dried (MgSO$_4$), filtered and evaporated. The residue was purified by chromatography (SiO$_2$, CH$_2$Cl$_2$/MeOH 40:1) to give 4.34 g (84%) 4-chloro-2-pyridin-4-yl-pyrimidine-5-carboxylic acid ethyl ester as a yellow solid, MS (EI): 263.1 (M$^+$).

b) 2-Pyridin-4-yl-4-o-tolyloxy-pyrimidine-5-carboxylic acid ethyl ester

A suspension of 0.6 g (2 28 mmol) 4-chloro-2-pyridin-4-yl-pyrimidine-5-carboxylic acid ethyl ester, 0.27 g (2 50 mmol) o-cresol and 2.97 g (9.10 mmol) Cs$_2$CO$_3$ in 15 ml acetonitrile was stirred for 17 h at RT. The suspension was poured into 150 ml H$_2$O and extracted three times with 90 ml ethyl acetate. The combined organic phases were dried (MgSO$_4$), filtered and evaporated. The residue was purified by chromatography (SiO2, ethyl acetate/MeOH 100:1) to give 0.74 g (97%) 2-pyridin-4-yl-4-o-tolyloxy-pyrimidine-5-carboxylic acid ethyl ester as a yellow solid, MS (EI): 335.1 (M$^+$).

c) 2-Pyridin-4-yl-4-o-tolyloxy-pyrimidine-5-carboxylic acid

To a solution of 0.70 g (2.08 mmol) 2-pyridin-4-yl-4-o-tolyloxy-pyrimidine-5-carboxylic acid ethyl ester in 20 ml ethanol a solution of 0.12 g (3.12 mmol) sodiumhydroxide in 10 ml water was added and the resulting mixture was stirred 2 h at RT. The pH of the solution was adjusted to 3 with 25% HCl. The mixture was extracted twice with CH$_2$Cl$_2$. The combined organic phases were dried (Na$_2$SO$_4$), filtered and evaporated. The resulting solid was triturated twice with 10 ml ethanol, filtered off and dried to give 0.60 g (94%) 2-pyridin-4-yl-4-o-tolyloxy-pyrimidine-5-carboxylic acid as a colorless solid, MS (EI): 307.1 (M$^+$).

d) 2-Pyridin-4-yl-4-o-tolyloxy-pyrimidine-5-carboxylic acid (3,5-bis-trifluoromethyl-benzyl)-methyl-amide To a solution of 0.35 g (1.14 mmol) 2-pyridin-4-yl-4-o-tolyloxy-pyrimidine-5-carboxylic acid in 20 ml CH$_2$Cl$_2$ 0.32 ml (2.28 mmol) triethylamine, 0.15 g (1.14 mmol) 1-hydroxy-benzotriazole and 0.22 g (1.14 mmol) N-(3-dimethylaminopropyl)-N'-ethylcarbodiimide hydrochloride 0.33 g (1.37 mmol) (3,5-bis-trifluormethyl-benzyl)-methyl-amin were added. The reaction mixture was stirred for 16 hrs. The reaction mixture was diluted with 20 ml CH$_2$Cl$_2$ and washed 50 ml H$_2$O. The organic layer was dried (MgSO$_4$), filtered and evaporated. The residue was purified by chromatography (SiO$_2$, CH$_2$Cl$_2$/MeOH 19:1) to give 0.33 g (53%) 2-pyridin-4-yl-4-o-tolyloxy-pyrimidine-5-carboxylic acid (3,5-bis-trifluoromethyl-benzyl)-methyl-amide as a colorless foam, MS (ISP): 547.1 (M+H)$^+$.

EXAMPLE 40

4-(4-Fluoro-phenoxy)-2-pyridin-4-yl-pyrimidine-5-carboxylic acid (3,5-bis-trifluoromethyl-benzyl)-methyl-amide In an analogous manner to that described in Example 39b) there was obtained from 4-chloro-2-pyridin-4-yl-pyrimidine-5-carboxylic acid ethyl ester and 4-fluorphenol 4-(4-fluoro-phenoxy)-2-pyridin-4-yl-pyrimidine-5-carboxylic acid ethyl ester, which was saponified as described in Example 39c) and reacted with (3,5-bis-trifluormethyl-benzyl)-methyl-amine to give as described in Example 39 d) 4-(4-fluoro-phenoxy)-2-pyridin-4-yl-pyrimidine-5-carboxylic acid (3,5-bis-trifluoromethyl-benzyl)-methyl-amide as a colorless foam, MS (ISP): 551.0 (M+H)$^+$.

EXAMPLE 41

2-Methyl-4-o-tolyloxy-pyrimidine-5-carboxylic acid (3,5-bis-trifluoromethyl-benzyl)-methyl-amide In an analogous manner to that described in Example 39b) there was obtained from 4-chloro-2-methyl-pyrimidine-5-carboxylic acid ethyl ester and o-cresol 2-methyl-4-o-tolyloxy-pyrimidine-5-carboxylic acid ethyl ester, which was saponified as described in Example 39c) and reacted with (3,5-bis-trifluormethyl-benzyl)-methyl-amine to give as described in Example 39d) 2-methyl-4-o-tolyloxy-pyrimidine-5-carboxylic acid (3,5-bis-trifluoromethyl-benzyl)-methyl-amide as a colorless foam, MS (EI): 483 (M$^+$).

EXAMPLE 42

2-Phenyl-4-o-tolyloxy-pyrimidine-5-carboxylic acid (3,5-bis-trifluoromethyl-benzyl)-methyl-amide In an analogous manner to that described in Example 39b) there was obtained from 4-chloro-2-phenyl-pyrimidine-5-carboxylic acid ethyl ester and o-cresol 2-phenyl-4-o-tolyloxy-pyrimidine-5-carboxylic acid ethyl ester, which was saponified as described in Example 39c) and reacted with (3,5-bis-trifluormethyl-benzyl)-methyl-amine to give as described in Example 39d) 2-phenyl-4-o-tolyloxy-pyrimidine-5-carboxylic acid (3,5-bis-trifluoromethyl-benzyl)-methyl-amide as a colorless foam, MS (ISP): 546.1 (M+H)$^+$.

EXAMPLE 43

4-o-Tolyloxy-[2,2' ]bipyrimidinyl-5-carboxylic acid (3,5-bis-trifluoromethyl-benzyl)-methyl-amide a) 4-Hydroxy-f2,21bipyrimidinyl-5-carboxylic acid ethyl ester To a fresh prepared solution of sodiumethanolate in ethanol (prepared from 0.44 g (18.92 mmol) Na in 20 ml Ethanol) 1.50 g (9.46 mmol) pyrimidine-2-carboxamidine hydrochloride was added. After 10 min. 1.89 ml (9.46 mmol) diethyl ethoxymethylenemalonate was added at 0° and the resulting suspension was stirred for 12 hrs. After addition of 20 ml H$_2$O, the pH was adjusted to 5 and the aqueous phase was extracted three times with CH$_2$Cl$_2$. The combined organic phases were dried (Na$_2$SO$_4$), filtered and evaporated. The residue was triturated with 5 ml diisopropylether, filtered off and dried to give 1.62 g (70%) 4-hydroxy-[2,2']bipyrimidinyl-5-carboxylic acid ethyl ester as a light yellow powder, MS (EI): 246.1 (M$^+$).

b) 4-Chloro-[2,2']bipyrimidinyl-5-carboxylic acid ethyl ester

A suspension of 1.62 g (6.5 mmol) 4-hydroxy-[2,2'] bipyrimidinyl-5-carboxylic acid ethyl ester in 16 ml POCl$_3$ was heated at reflux for 1h. The solution was cooled to RT and poured into 100 ml ice-water. The pH of the solution was adjusted to 8 with sat. NaHCO$_3$-solution. The water phase was extracted three times with 80 ml CH$_2$Cl$_2$. The combined organic phases were dried (Na$_2$SO$_4$), filtered and evaporated. The residue was purified by chromatography (SiO$_2$, CH$_2$Cl$_2$/MeOH 95:5) to give 1.43 g (82%) 4-chloro-[2,2']bipyrimidinyl-5-carboxylic acid ethyl ester as a light brown solid, MS (EI): 264.1 (M$^+$).

c) 4-o-Tolyloxy-f2,21bipyrimidinyl-5-carboxylic acid ethyl ester

To a solution of 1.43 g (5.4 mmol) 4-chloro-[2,2'] bipyrimidinyl-5-carboxylic acid ethyl ester in 35 ml acetonitrile 0.5 g (7.0 mmol) o-cresol and 7.0 g (21.6 mmol) Cs$_2$CO$_3$ were added and the reaction mixture stirred for 14 hrs at RT. The suspension was poured into ice-water and extracted two times with CH$_2$Cl$_2$. The combined organic phases were dried (Na$_2$SO$_4$), filtered and evaporated. The residue was purified by chromatography (SiO$_2$, CH$_2$Cl$_2$/MeOH 19:1) to give 0.96 g (53%) 4-o-tolyloxy-[2,2'] bipyrimidinyl-5-carboxylic acid ethyl ester as a light yellow solid, MS (ISP): 337.2 (M+H)$^+$.

d) 4-o-Tolyloxy-[2,2']bipyrimidinyl-5-carboxylic acid

To a solution of 0.33 g (0.98 mmol) 4-o-tolyloxy-[2,2'] bipyrimidinyl-5-carboxylic acid ethyl ester in 15 ml ethanol 3.68 ml 0.4 N NaOH was added and the resulting solution was stirred for 2 hrs at RT. The pH of the solution was adjusted to 4 with 1N HCl. The aqueous solution was extracted three times with CH$_2$Cl$_2$. The combined organic phases were dried (Na$_2$SO$_4$), filtered and evaporated. The resulting solid was triturated twice with diethyl ether, filtered off and dried to give 0.26 g (85%) 4-o-tolyloxy-[2,2'] bipyrimidinyl-5-carboxylic acid as a light yellow solid, MS (ISN): 307.3 (M–H)$^-$.

e) 4-o-Tolyloxy-[2,2']bipyrimidinyl-5-carboxylic acid (3,5-bis-trifluoromethyl-benzyl)-methyl-amide To a solution of 0.25 g (0.83 mmol) 4-o-tolyloxy-[2,2'] bipyrimidinyl-5-carboxylic acid in 15 ml CH$_2$Cl$_2$, 0.23 ml (1.6 mmol) triethylamine, 0.13 g (0.83 mmol) 1-hydroxybenzotriazole and 0.16 g (0.83 mmol) N-(3-dimethylaminopropyl)-N'-ethylcarbodiimide hydrochloride 0.25 g (1 mmol)(3,5-bis-trifluormethyl-benzyl)methyl-amin were added. The reaction mixture was stirred for 16 hrs. The reaction mixture was diluted with 20 ml CH$_2$Cl$_2$, washed with 50 ml 0.5N HCl and 50 ml CH$_2$Cl$_2$. The combined organic layers were dried (MgSO$_4$), filtered and evaporated. The residue was purified by chromatography (SiO$_2$, CH$_2$Cl$_2$/MeOH 19:1) to give 0.39 g (86%) 4-o-tolyloxy-[2,2'] bipyrimidinyl-5-carboxylic acid (3,5-bis-trifluoromethyl-benzyl)-methyl-amide as a light yellow foam, MS (ISP): 548.1 (M+H)$^+$.

EXAMPLE 44

2-Thiomorpholin-4-yl-4-o-tolyloxy-pyrimidine-5-carboxylic acid (3,5-bis-trifluoromethyl-benzyl)-methyl-amide To a solution of 0.79g (1.44 mmol) 2-methansulfonyl-4-o-tolyloxy-pyrimidine-5-carboxylic acid (3,5-bis-trifluoromethyl-benzyl)-methyl-amide in 40 ml dioxane 0.34 ml (3.6 mmol) thiomorpholine was added. The reaction mixture was stirred for 16 hrs. After evaporation of the solvent, the residue was distributed between 50 ml CH$_2$Cl$_2$ and 50 ml H$_2$O. The aqueous layer was extracted with 50 ml CH$_2$Cl$_2$, the combined organic layers dried (MgSO$_4$), filtered and evaporated. The residue was purified by chromatography (SiO$_2$, CH$_2$Cl$_2$/MeOH 40:1) to give 0.48 g (59%) 2-thiomorpholin-4-yl-4-o-tolyloxy-pyrimidine-5-carboxylic acid (3,5-bis-trifluoromethyl-benzyl)-methyl-amide as a colorless solid, MS (ISP): 571.1 (M+H)$^+$.

EXAMPLE 45

2-(1,1-Dioxo-1$\lambda^6$-thiomorpholin-4-yl)-4-o-tolyloxy-pyrimidine-5-carboxylic acid (3,5-bis-trifluoromethyl-benzyl)-methyl-amide To a solution of 0.44 g (0.77 mmol) 2-thiomorpholin-4-yl-4-o-tolyloxy-pyrimidine-5-carboxylic acid (3,5-bis-trifluoromethyl-benzyl)-methyl-amide in 25 ml CH$_2$Cl$_2$ 0.48 g (1.93 mmol) 3-chloroperbenzoicacid (70%) was added at 5° and the reaction mixture was stirred for 1 h at RT. After addition of 50 ml sat. NaHCO$_3$-solution, the layers were separated, the organic phase washed with NaHCO$_3$-solution, dried (Na$_2$SO$_4$), filtered and evaporated. The residue was purified by chromatography (SiO$_2$, CH$_2$Cl$_2$/ethyl acetate 4:1) to give 0.42 g (91%) 2-(1,1-dioxo-1$\lambda^6$-thiomorpholin-4-yl)-4-o-tolyloxy-pyrimidine-5-carboxylic acid (3,5-bis-trifluoromethyl-benzyl)-methyl-amide as a colorless solid, MS (ISP): 602.9(M+H)$^+$.

EXAMPLE 46

2-(3,5-Bis-trifluoromethyl-phenyl)-N-methyl-N-(2-methylsulfanyl-4-o-tolyloxy-pyrimidin-5-yl)-isobutyramide a) (2-Methylsulfanyl-4-o-tolyloxy-pyrimidin-5-yl)-carbamic acid tert.-butyl ester To a solution of 1.90 g (6.88 mmol) 2-methylsulfanyl-4-o-tolyloxy-pyrimidine-5-carboxylic acid, 0.95 ml triethylamine (6.88 mmol) and 1.29 ml (1.37 mmol) t-butanol in 25 ml THF, 1.47 ml (6.88 mmol) diphenylphosphorylazide were added and the resulting solution heated at reflux for 12 hrs. After evaporation of the solvent, the residue was distributed between CH$_2$Cl$_2$ and H$_2$O. The aquoeus phase was extracted twice with 80 ml CH$_2$Cl$_2$. The combined organic layers were dried (Na$_2$SO$_4$), filtered and evaporated. The residue was purified by chromatography (SiO$_2$, CH$_2$Cl$_2$, ethyl acetate 40:1) to give 1.70 g (71%) (2-methylsulfanyl-4-o-tolyloxy-pyrimidin-5-yl)-carbamic acid tert.-butyl ester as a colorless solid, MS (ISP): 348.2 (M+H)$^+$.

b) Methyl-(2-methylsulfanyl-4-o-tolyloxy-pyrimidin-5-yl)-carbamic acid tert-butyl ester To a solution of 1.60 g (4.61 mmol) (2-methylsulfanyl-4-o-tolyloxy-pyrimidin-5-yl)-carbamic acid tert.-butyl ester in 20 ml N,N-dimethylformamide 0.25 g (6.4 mmol) sodiumhydride (60% dispersion in mineraloil) was added and the reaction mixture stirred for 1 h. After the addition of 0.48 ml (7.83 mmol) methyl iodide at 0°, the reaction mixture was stirred for 3 hrs. The reaction mixture was poured into 100 ml ice-water and three times extracted with 80 ml CH$_2$Cl$_2$. The combined organic layers were dried (Na$_2$SO$_4$), filtered and evaporated. The residue was purified by chromatography (SiO$_2$, CH$_2$Cl$_2$/ethyl acetate 19:1) to give 1.60 g (98%) methyl-(2-methylsulfanyl-4-o-tolyloxy-pyrimidin-5-yl)-carbamic acid tert-butyl ester as a colorless oil, MS (EI): 361 (M$^+$)

c) Methyl-(2-methylsulfanyl-4-o-tolyloxy-pyrimidin-5-yl)-amine

To a solution of 1.60 g (4.43 mmol) methyl-(2-methylsulfanyl-4-o-tolyloxy-pyrimidin-5-yl)-carbamic acid tert.-butyl ester in 20 ml CH$_2$Cl$_2$ 2 ml trifluoracetic acid was added and the reaction mixture stirred for 2 hrs. at 40°. The reaction mixture was poured into ice-water and the pH of the solution adjusted to 10 with 1N NaOH solution. The aqueous phase was extracted three times with 80 ml CH$_2$Cl$_2$. The combined organic layers were dried (Na$_2$SO$_4$), filtered and evaporated to give 1.10 g (95%) methyl-(2-methylsulfanyl-4-o-tolyloxy-pyrimidin-5-yl)-amine as a white solid, MS (EI): 261 (M$^+$).

d) 2-(3,5-Bis-trifluoromethyl-phenyl)-N-methyl-N-(2-methylsulfanyl-4-o-tolyloxy pyrimidin-5-yl)-isobutyramide To a solution of 1.10 g (4.21 mol) methyl-(2-methylsulfanyl-4-o-tolyloxy-pyrimidin-5-yl)-amine and 1.44 ml (8.42 mmol) N-ethyldiisopropylamine in 30 ml CH$_2$Cl$_2$ a solution of 1.87 g (5.89 mmol) 2-(3,5-bis-trifluormethyl-phenyl)-2-methyl-propionyl chloride in 5 ml CH$_2$Cl$_2$ was added and the reaction mixture stirred for 12 hrs at RT. The reaction mixture was poured into 50 ml 0.5 N NaOH-solution. The phases were separated and the aqueous phase three times extracted with 80 ml CH$_2$Cl$_2$. The combined organic layers were dried (Na$_2$SO$_4$), filtered and evaporated. The residue was purified by chromatography (SiO$_2$, hexane/ ethyl acetate 2:1) to give 2.10 g (92%) 2-(3,5-bis-trifluoromethyl-phenyl)-N-methyl-N-(2-methylsulfanyl-4-o-tolyloxy-pyrimidin-5-yl)-isobutyramide as a white foam, MS (ISP): 544.2 (M+H)$^+$.

EXAMPLE 47

2-(3,5-Bis-trifluoromethyl-phenyl)-N-(2-methanesulfonyl-4-o-tolyloxy-pyrimidin-5-yl)-N-methyl-isobutyramide To a solution of 2.00 g (3.68 mmol) 2-(3,5-bis-trifluoromethyl-phenyl)-N-methyl-N-(2-methylsulfanyl-4-o-tolyloxy-pyrimidin-5-yl)-isobutyramide in 80 ml CH$_2$Cl$_2$ 2.26 g (9.20 mmol) 3-chloroperbenzoic acid (70%) was added at 5° and the reaction mixture stirred for 2 hrs. at RT. After addition of 150 ml sat. NaHCO$_3$-solution, the layers were separated, the organic phase washed with sat. NaHCO$_3$-solution, dried (Na$_2$SO$_4$), filtered and evaporated. The residue was purified by chromatography (SiO$_2$, CH$_2$Cl$_2$/ethyl acetate 19:1) to give 1.90 g (83%) 2-(3,5-bis-trifluoromethyl-phenyl)-N-(2-methanesulfonyl-4-o-tolyloxy-pyrimidin-5-yl)-N-methyl-isobutyramide as a white foam, MS (EI): 575 (M$^+$).

EXAMPLE 48

2-(3,5-Bis-trifluoromethyl-phenyl)-N-methyl-N-(2-morpholin-4-yl-4-o-tolyloxy-pyrimidin-5-yl)-isobutyramide To a solution of 0.2 g (0.35 mmol) 2-(3,5-bis-trifluoromethyl-phenyl)-N-(2-methanesulfonyl-4-o-tolyloxy-pyrimidin-5-yl)-N-methyl-isobutyramide in 10 ml dioxane 0.076 ml (0.87 mmol) morpholine was added. The reaction mixture was stirred for 16 hrs. After evaporation of the solvent, the residue was distributed between 50 ml CH$_2$Cl$_2$ and 50 ml sat. NaHCO$_3$-solution. The aqueous layer was extracted with 50 ml CH$_2$Cl$_2$, the combined organic layers dried (MgSO$_4$), filtered and evaporated. The residue was purified by chromatography (SiO$_2$, CH$_2$Cl$_2$/methanol 50:1) to give 0.17 g (84%) 2-(3,5-bis-trifluoromethyl-phenyl)-N-methyl-N-(2-morpholin-4-yl-4-o-tolyloxy-pyrimidin-5-yl)-isobutyramide as a white foam, MS (ISP): 583.2 (M+H)$^+$.

EXAMPLE 49

2-(3,5-Bis-trifluoromethyl-phenyl)-N-methyl-N-[2-(4-methyl-piperazin-1-yl)-4-o-tolyloxy-pyrimidin-5-yl]-isobutyramide To a solution of 0.22 g (0.38 mmol) 2-(3,5-bis-trifluoromethyl-phenyl)-N-(2-methanesulfonyl-4-o-tolyloxy-pyrimidin-5-yl)-N-methyl-isobutyramide in 10 ml dioxane 0.106 ml (0.96 mmol) I-methylpiperazine was added. The reaction mixture was stirred for 16 hrs. After evaporation of the solvent, the residue was distributed between 50 ml CH$_2$Cl$_2$ and 50 ml sat. NaHCO$_3$-solution. The aqueous layer was extracted with 50 ml CH$_2$Cl$_2$, the combined organic layers dried (MgSO$_4$), filtered and evaporated. The residue was purified by chromatography (SiO$_2$, CH$_2$Cl$_2$/MeOH/NH$_4$OH 110:10:1) to give 0.11 g (48%) 2-(3,5-bis-trifluoromethyl-phenyl)-N-methyl-N-[2-(4-methyl-piperazin-1-yl)-4-o-tolyloxy-pyrimidin-5-yl]-isobutyramide as a white foam, MS (ISP): 596.2 (M+H)$^+$.

EXAMPLE 50

2-(3,5-Bis-trifluoromethyl-phenyl)-N-methyl-N-(2-piperazin-1-yl-4-o-tolyloxy-pyrimidin-5-yl)-isobutyramide To a solution of 0.30 g (0.52 mmol) 2-(3,5-bis-trifluoromethyl-phenyl)-N-(2-methanesulfonyl-4-o-tolyloxy-pyrimidin-5-yl)-N-methyl-isobutyramide in 10 ml dioxane 0.112 g (1.3 mmol) piperazine was added. The reaction mixture was stirred for 16 hrs. After evaporation of the solvent, the residue was distributed between 50 ml CH$_2$Cl$_2$ and 50 ml sat. NaHCO$_3$-solution. The aqueous layer was extracted with 50 ml CH$_2$Cl$_2$, the combined organic layers dried (MgSO$_4$), filtered and evaporated. The residue was purified by chromatography (SiO$_2$, CH$_2$Cl$_2$/MeOH/NH$_4$OH 140:10:1) to give 0.20 g (66%) 2-(3,5-bis-trifluoromethyl-phenyl)-N-methyl-N-(2-piperazin-1-yl-4-o-tolyloxy-pyrimidin-5-yl)-isobutyramide as a white foam, MS (ISP): 582.2 (M+H)$^+$.

EXAMPLE 51

2-(3,5-Bis-trifluoromethyl-phenyl)-N-[2-(2-dimethylamino-ethylamino)-4-o-tolyloxy-pyrimidin-5-yl]-N-methyl-isobutyramide To a solution of 0.25 g (0.43 mmol) 2-(3,5-bis-trifluoromethyl-phenyl)-N-(2-methanesulfonyl-4-o-tolyloxy-pyrimidin-5-yl)-N-methyl-isobutyramide in 10 ml dioxan 0.119 ml (1.09 mmol) 2-dimethylaminoethylamine was added. The reaction mixture was stirred for 16 hrs. After evaporation of the solvent, the residue was distributed between 50 ml CH$_2$Cl$_2$ and 50 ml sat. NaHCO$_3$-solution. The aqueous layer was extracted with 50 ml CH$_2$Cl$_2$, the combined organic layers dried (MgSO$_4$), filtered and evaporated. The residue was purified by chromatography (SiO$_2$, CH$_2$Cl$_2$/methanol/NH$_4$OH 140:10:1) to give 0.20 g (79%) 2-(3,5-bis-trifluoromethyl-phenyl)-N-[2-(2-dimethylamino-ethylamino)-4-o-tolyloxy-pyrimidin-5-yl]-N-methyl-isobutyramide as a white foam, MS (ISP): 584.2 (M+H)$^+$.

EXAMPLE 52

2-(3,5-Bis-trifluoromethyl-phenyl)-N-methyl-N-[2-(2-morpholin-4-yl-ethoxy)-4-o-tolyloxy-pyrimidin-5-yl]-isobutyramide To a solution of 0.4 g (0.7 mmol) 2-(3,5-bis-trifluoromethyl-phenyl)-N-(2-methanesulfonyl-4-o-tolyloxy-pyrimidin-5-yl)-N-methyl-isobutyramide in 20 ml acetonitrile 0.126 ml (1.04 mmol) N-(2-hydroxyethyl) morpholine and 1.13 g (3.48 mmol) Cs$_2$CO$_3$ were added. The reaction mixture was stirred for 16 hrs. After evaporation of the solvent, the residue was distributed between 50 ml CH$_2$Cl$_2$ and 50 ml H$_2$O. The aqueous layer was extracted with 50 ml CH$_2$Cl$_2$, the combined organic layers dried (MgSO$_4$), filtered and evaporated. The residue was purified by chromatography (SiO$_2$, CH$_2$Cl$_2$/MeOH 40:1) to give 0.30 g (69%) 2-(3,5-bis-trifluoromethyl-phenyl)-N-methyl-N-[2-(2-morpholin-4-yl-ethoxy)-4-o-tolyloxy-pyrimidin-5-yl]-isobutyramide as a colorless foam, MS (ISP): 627.2 (M+H)$^+$.

EXAMPLE 53

2-(3,5-Bis-trifluoromethyl-phenyl)-N-[2-(2-dimethylamino-ethoxy)-4-o-tolyloxy-pyrimidin-5-yl]-N-methyl-isobutyramide To a solution of 0.25 g (0.43 mmol) 2-(3,5-bis-trifluoromethyl-phenyl)-N-(2-methanesulfonyl-4-o- tolyloxy-pyrimidin-5-yl)-N-methyl-isobutyramide in 10 ml acetonitrile 0.066 ml (0.65 mmol) 2-dimethylaminoethanol and 0.70 g (2.14 mmol) $Cs_2CO_3$ were added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/MeOH/$NH_4OH$ 110:10:1) to give 0.18 g (71%) 2-(3,5-bis-trifluoromethyl-phenyl)-N-[2-(2-dimethylamino-ethoxy)-4-o-tolyloxy-pyrimidin-5-yl]-N-methyl-isobutyramide as a colorless foam, MS (ISP): 585.2 $(M+H)^+$.

EXAMPLE 54

2-(3,5-Bis-trifluoromethyl-phenyl)-N-[2-(3-dimethylamino-propoxy)-4-o-tolyloxy-pyrimidin-5-yl]-N-methyl-isobutyramide To a solution of 0.30 g (0.52 mmol) 2-(3,5-bis-trifluoromethyl-phenyl)-N-(2-methanesulfonyl-4-o-tolyloxy-pyrimidin-5-yl)-N-methyl-isobutyramide in 20 ml acetonitrile 0.061 ml (0.78 mmol) 2-dimethylaminopropanol and 0.85 g (2.61 mmol) $Cs_2CO_3$ were added. The reaction mixture was stirred for 16 hrs. After evaporation of the solvent, the residue was distributed between 50 ml $CH_2Cl_2$ and 50 ml $H_2O$. The aqueous layer was extracted with 50 ml $CH_2Cl_2$, the combined organic layers dried ($MgSO_4$), filtered and evaporated. The residue was purified by chromatography ($SiO_2$, $CH_2Cl_2$/MeOH/$NH_4OH$ 140:10:1) to give 0.20 g (64%) 2-(3,5-bis-trifluoromethyl-phenyl)-N-[2-(2-dimethylamino-propoxy)-4-o-tolyloxy-pyrimidin-5-yl]-N-methyl-isobutyramide as a colorless oil, MS (ISP): 599.2 $(M+H)^+$.

EXAMPLE 55

2-(3,5-Bis-trifluoromethyl-phenyl)-N-[4-(4-fluoro-phenoxy)-2-methylsulfanyl-pyrimidin-5-yl]-N-methyl-isobutyramide In an analougous manner to that described in Examle 46 a) there was obtained from 4-(4-fluoro-phenoxy)-2-methylsulfanyl-pyrimidine-5-carboxylic acid, diphenylphosporylazide and t-butanol [4-(4-fluoro-phenoxy)-2-methylsulfanyl-pyrimidin-5-yl]-carbamic acid tert.-butyl ester, which was methylated with methyliodide and than deprotected with trifluoracetic acid according to Example 43b)c). The resulting [4-(4-fluoro-phenoxy)-2-methylsulfanyl-pyrimidin-5-yl]-methyl-amine was treated with 2-(3,5-bis-trifluormethyl-phenyl)-2-methyl-propionyl chloride as described in Example 43e) to give 2-(3,5-bis-trifluoromethyl-phenyl)-N-[4-(4-fluoro-phenoxy)-2-methylsulfanyl-pyrimidin-5-yl]-N-methyl-isobutyramide as a white foam, MS (EI): 547 $(M^+)$.

EXAMPLE 56

2-(3,5-Bis-trifluoromethyl-phenyl)-N-[4-(4-fluoro-phenoxy)-2-methanesulfonyl-pyrimidin-5-yl]-N-methyl-isobutyramide In an analogous manner to that described in Example 47 there was obtained from 2-(3,5-bis-trifluoromethyl-phenyl)-N-[4-(4-fluoro-phenoxy)-2-methylsulfanyl-pyrimidin-5-yl]-N-methyl-isobutyramide and 3-chloroperbenzoic acid 2-(3,5-bis-trifluoromethyl-phenyl)-N-[4-(4-fluoro-phenoxy)-2-methanesulfonyl-pyrimidin-5-yl]-N-methyl-isobutyramide as a white foam, MS (ISP): 580.2 $(M+H)^+$.

EXAMPLE 57

2-(3,5-Bis-trifluoromethyl-phenyl)-N-[4-(4-fluoro-phenoxy)-2-morpholin-4-yl-pyrimidin-5-yl]-N-methyl-isobutyramide In an analogous manner to that described in Example 48 there was obtained from 2-(3,5-bis-trifluoromethyl-phenyl)-N-[4-(4-fluoro-phenoxy)-2-methanesulfonyl-pyrimidin-5-yl]-N-methyl-isobutyramide and morpholine 2-(3,5-bis-trifluoromethyl-phenyl)-N-[4-(4-fluoro-phenoxy)-2-morpholin-4-yl-pyrimidin-5-yl]-N-methyl-isobutyramide as a colorless foam, MS (ISP): 587.2 $(M+H)^+$.

EXAMPLE 58

2-(3,5-Bis-trifluoromethyl-phenyl)-N-[4-(4-fluoro-phenoxy)-2-(4-methyl-piperazin-1-yl)-pyrimidin-5-yl]-N-methyl-isobutyramide In an analogous manner to that described in Example 49there was obtained from 2-(3,5-bis-trifluoromethyl-phenyl)-N-[4-(4-fluoro-phenoxy)-2-methanesulfonyl-pyrimidin-5-yl]-N-methyl-isobutyramide and 1-methylpiperazine 2-(3,5-bis-trifluoromethyl-phenyl)-N-[4-(4-fluoro-phenoxy)-2-(4-methyl-piperazin-1-yl)-pyrimidin-5-yl]-N-methyl-isobutyramide as a colorless foam, MS (ISP): 600.1 $(M+H)^+$.

EXAMPLE 59

2-(3,5-Bis-trifluoromethyl-phenyl)-N-[4-(4-fluoro-phenoxy)-2-piperazin-1-yl-pyrimidin-5-yl]-N-methyl-isobutyramide In an analogous manner to that described in Example 50 there was obtained from 2-(3,5-bis-trifluoromethyl-phenyl)-N-[4-(4-fluoro-phenoxy)-2-methanesulfonyl-pyrimidin-5-yl]-N-methyl-isobutyramide and piperazine 2-(3,5-bis-trifluoromethyl-phenyl)-N-[4-(4-fluoro-phenoxy)-2-piperazin-1-yl-pyrimidin-5-yl]-N-methyl-isobutyramide as a colorless foam, MS (ISP): 586.2 $(M+H)^+$.

EXAMPLE 60

2-(3,5-Bis-trifluoromethyl-phenyl)-N-[2-(2-dimethylamino-ethylamino)-4-(4-fluoro-phenoxy)-pyrimidin-5-yl]-N-methyl-isobutyramide In an analogous manner to that described in Example 51 there was obtained from 2-(3,5-bis-trifluoromethyl-phenyl)-N-[4-(4-fluoro-phenoxy)-2-methanesulfonyl-pyrimidin-5-yl]-N-methyl-isobutyramide and 2-dimethylaminoethylamine 2-(3,5-bis-trifluoromethyl-phenyl)-N-[2-(2-dimethylamino-ethylamino)-4-(4-fluoro-phenoxy)-pyrimidin-5-yl]-N-methyl-isobutyramide as a colorless foam, MS (ISP): 588.3$(M+H)^+$.

EXAMPLE 61

2-(3,5-Bis-trifluoromethyl-phenyl)-N-[4-(4-fluoro-phenoxy)-2-(2-morpholin-4-yl-ethoxy)-pyrimidin-5-yl]-N-methyl-isobutyramide In an analogous manner to that described in Example 52 there was obtained from 2-(3,5-bis-trifluoromethyl-phenyl)-N-[4-(4-fluoro-phenoxy)-2-methanesulfonyl-pyrimidin-5-yl]-N-methyl-isobutyramide and N-(2-hydroxyethyl) morpholine 2-(3,5-bis-trifluoromethyl-phenyl)-N-[4-(4-fluoro-phenoxy)-2-(2-morpholin-4-yl-ethoxy)-pyrimidin-5- yl]-N-methyl-isobutyramide as a colorless foam, MS (ISP): 631.1 (M+H)+.

EXAMPLE 62

2-(3,5-Bis-trifluoromethyl-phenyl)-N-[2-(2-dimethylamino-ethoxy)-4-(4-fluoro-phenoxy)-pyrimidin-5-yl]-N-methyl-isobutyramide In an analogous manner to that described in Example 53 there was obtained from 2-(3,5-bis-trifluoromethyl-phenyl)-N-[4-(4-fluoro-phenoxy)-2-methanesulfonyl-pyrimidin-5-yl]-N-methyl-isobutyramide and 2-dimethylaminoethanol 2-(3,5-bis-trifluoromethyl-phenyl)-N-[2-(2-dimethylamino-ethoxy)-4-(4-fluoro-phenoxy)-pyrimidin-5-yl]-N-methyl-isobutyramide as a colorless foam, MS (ISP): 589.2 (M+H)+.

EXAMPLE 63

2-(3,5-Bis-trifluoromethyl-phenyl)-N-[2-(3-dimethylamino-propoxy)-4-(4-fluoro-phenoxy)-pyrimidin-5-yl]-N-methyl-isobutyramide In an analogous manner to that described in Example 54 there was obtained from 2-(3,5-bis-trifluoromethyl-phenyl)-N-[4-(4-fluoro-phenoxy)-2-methanesulfonyl-pyrimidin-5-yl]-N-methyl-isobutyramide and 2-dimethylaminopropanol 2-(3,5-bis-trifluoromethyl-phenyl)-N-[2-(2-dimethylamino-ethoxy)-4-(4-fluoro-phenoxy)-pyrimidin-5-yl]-N-methyl-isobutyramide as a colorless foam, MS (ISP): 603.1 (M+H)+.

EXAMPLE 64

2-(3,5-Bis-trifluoromethyl-phenyl)-N-[4-(2-chloro-phenoxy)-2-methylsulfanyl-pyrimidin-5-yl]-N-methyl-isobutyramide In an analougous manner to that described in Examle 46 a) there was obtained from 4-(2-chloro-phenoxy)-2-methylsulfanyl-pyrimidine-5-carboxylic acid, diphenylphosphorylazide and t-butanol [4-(2-chloro-phenoxy)-2-methylsulfanyl-pyrimidin-5-yl]-carbamic acid tert.-butyl ester, which was methylated with methyliodide and than deprotected whit trifluoracetic acid according to Example 43b)
c). The resulting [4-(2-chloro-phenoxy)-2-methylsulfanyl-pyrimidin-5-yl]-methyl-amine was treated with 2-(3,5-bis-trifluormethyl-phenyl)-2-methyl-propionyl chloride as described in Example 43e) to give 2-(3,5-bis-trifluoromethyl-phenyl)-N-[4-(2-chloro-phenoxy)-2-methylsulfanyl-pyrimidin-5-yl]-N-methyl-isobutyramide as a white foam, MS (ISP): 564.2 (M+H)+.

EXAMPLE 65

2-(3,5-Bis-trifluoromethyl-phenyl)-N-[4-(2-chloro-phenoxy)-2-methanesulfonyl-pyrimidin-5-yl]-N-methyl-isobutyramide In an analogous manner to that described in Example 47 there was obtained from 2-(3,5-bis-trifluoromethyl-phenyl)-N-[4-(2-chloro-phenoxy)-2-methylsulfanyl-pyrimidin-5-yl]-N-methyl-isobutyramide and 3-chloroperbenzoic acid 2-(3,5-bis-trifluoromethyl-phenyl)-N-[4-(2-chloro-phenoxy)-2-methanesulfonyl-pyrimidin-5-yl]-N-methyl-isobutyramide as a white foam, MS (ISP): 596.1 (M+H)+.

EXAMPLE 66

2-(3,5-Bis-trifluoromethyl-phenyl)-N-[4-(2-chloro-phenoxy)-2-morpholin-4-yl-pyrimidin-5-yl]-N-methyl-isobutyramide In an analogous manner to that described in Example 48 there was obtained from 2-(3,5-bis-trifluoromethyl-phenyl)-N-[4-(2-chloro-phenoxy)-2-methanesulfonyl-pyrimidin-5-yl]-N-methyl-isobutyramide and morpholine 2-(3,5-bis-trifluoromethyl-phenyl)-N-[4-(2-chloro-phenoxy)-2-morpholin-4-yl-pyrimidin-5-yl]-N-methyl-isobutyramide as a colorless foam, MS (ISP): 603.0 (M+H)+.

EXAMPLE 67

2-(3,5-Bis-trifluoromethyl-phenyl)-N-[4-(2-chloro-phenoxy)-2-(4-methyl-piperazin-1-yl)-pyrimidin-5-yl]-N-methyl-isobutyramide In an analogous manner to that described in Example 49there was obtained from 2-(3,5-bis-trifluoromethyl-phenyl)-N-[4-(2-chloro-phenoxy)-2-methanesulfonyl-pyrimidin-5-yl]-N-methyl-isobutyramide and 1-methylpiperazine 2-(3,5-bis-trifluoromethyl-phenyl)-N-[4-(2-chloro-phenoxy)-2-(4-methyl-piperazin-1-yl)-pyrimidin-5-yl]-N-methyl-isobutyramide as a colorless foam, MS (ISP): 616.1 (M+H)+.

EXAMPLE 68

2-(3,5-Bis-trifluoromethyl-phenyl)-N-[4-(2-chloro-phenoxy)-2-piperazin-1-yl-pyrimidin-5-yl]-N-methyl-isobutyramide In an analogous manner to that described in Example 50 there was obtained from 2-(3,5-bis-trifluoromethyl-phenyl)-N-[4-(2-chloro-phenoxy)-2-methanesulfonyl-pyrimidin-5-yl]-N-methyl-isobutyramide and piperazine 2-(3,5-bis-trifluoromethyl-phenyl)-N-[4-(2-chloro-phenoxy)-2-piperazin-1-yl-pyrimidin-5-yl]-N-methyl-isobutyramide as a colorless foam, MS (ISP): 602.1 (M+H)+.

EXAMPLE 69

2-(3,5-Bis-trifluoromethyl-phenyl)-N-[4-(2-chloro-phenoxy)-2-(2-morpholin-4-yl-ethoxy)-pyrimidin-5-yl]-N-methyl-isobutyramide In an analogous manner to that described in Example 52 there was obtained from 2-(33,5-bis-trifluoromethyl-phenyl)-N-[4-(2-chloro-phenoxy)-2-methanesulfonyl-pyrimidin-5-yl]-N-methyl-isobutyramide and N-(2-hydroxyethyl)morpholine 2-(3,5-bis-trifluoromethyl-phenyl)-N-[4-(2-chloro-phenoxy)-2-(2-morpholin-4-yl-ethoxy)-pyrimidin-5-yl]-N-methyl-isobutyramide as a colorless foam, MS (ISP): 647.1 (M+H)+.

EXAMPLE 70

2-(3,5-Bis-trifluoromethyl-phenyl)-N-[2-(2-dimethylamino-ethoxy)-4-(2-chloro-phenoxy)-pyrimidin-5-yl]-N-methyl-isobutyramide In an analogous manner to that described in Example 53there was obtained from 2-(3,5-bis-trifluoromethyl-phenyl)-N-[4-(2-chloro-phenoxy)-2-methanesulfonyl-pyrimidin-5-yl]-N-methyl-isobutyramide and 2-dimethylaminoethanol 2-(3,5-bis-trifluoromethyl-phenyl)-N-[2-(2-dimethylamino-ethoxy)-4-(2-chloro-phenoxy)-pyrimidin-5-yl]-N-methyl-isobutyramide as a colorless foam, MS (ISP): 605.0 (M+H)+.

EXAMPLE 71

2-(3,5-Bis-trifluoromethyl-phenyl)-N-[2-(3-dimethylamino-propoxy)-4-(2-chloro-phenoxy)-pyrimidin-5-yl]-N-methyl-isobutyramide In an analogous manner to that described in Example 54 there was obtained from 2-(3,5-bis-trifluoromethyl-phenyl)-

N-[4-(2-chloro-phenoxy)-2-methanesulfonyl-pyrimidin-5-yl]-N-methyl-isobutyramide and 2-dimethylaminopropanol 2-(3,5-bis-trifluoromethyl-phenyl)-N-[2-(2-dimethylamino-ethoxy)-4-(2-chloro-phenoxy)-pyrimidin-5-yl]-N-methyl-isobutyramide as a colorless foam, MS (ISP): 619.1 (M+H)$^+$

EXAMPLE 72

2-(3,5-Bis-trifluoromethyl-phenyl)-N-methyl-N-(2-methyl-4-o-tolyloxy-pyrimidin-5-yl)-isobutyramide a) (2-Methyl-4-o-tolyloxy-pyrimidin-5-yl)-carbamic acid tert.-butyl ester To a solution of 2.50 g (10.24 mmol) 2-methyl-4-o-tolyloxy-pyrimidine-5-carboxylic acid, 1.43 ml triethylamine (10.24 mmol) and 1.9 ml (20.4 mmol) t-butanol in 50 ml THF, 2.2 ml (10.24 mmol) diphenylphosporylazide were added and the resulting solution heated at reflux for 12 hrs. After evaporation of the solvent, the residue was distributed between CH$_2$Cl$_2$ and H$_2$O. The aquoeus phase was extracted twice with 80 ml CH$_2$Cl$_2$. The combined organic layers were dried (Na$_2$SO$_4$), filtered and evaporated. The residue was purified by chromatography (SiO$_2$, CH$_2$Cl$_2$/MeOH 40:1) to give 1.83 g (56%) (2-methyl-4-o-tolyloxy-pyrimidin-5-yl)-carbamic acid tert.-butyl ester as a colorless solid, MS (ISP): 316.3 (M+H)$^+$.

b) Methyl-(2-methyl-4-o-tolyloxy-pyrimidin-5-yl)-carbamic acid tert.-butyl ester To a solution of 1.83g (5.80 mmol) (2-methyl-4-o-tolyloxy-pyrimidin-5-yl)-carbamic acid tert.-butyl ester in 25 ml N,N-dimethylformamide 0.35 g (68.7 mmol) sodiumhydride (60% dispersion in mineraloil) was added and the reaction mixture stirred for 1 h. After the addition of 0.65 ml (10.4 mmol) methyl iodide at 0°, the reaction mixture was stirred for 2 hrs. The reaction mixture was poured into 100 ml ice-water and three times extracted with 80 ml CH$_2$Cl$_2$. The combined organic layers were dried (Na$_2$SO$_4$), filtered and evaporated. The residue was purified by chromatography (SiO$_2$, CH$_2$Cl$_2$/ethyl acetate 40:1) to give 1.90 g (99%) methyl-(2-methyl-4-o-tolyloxy-pyrimidin-5-yl)-carbamic acid tert.-butyl ester as a colorless oil, MS (ISP): 330.4 (M+H)$^+$.

c) Methyl-(2-methyl-4-o-tolyloxy-pyrimidin-5-yl)-amine

To a solution of 1.90 g (5.77 mmol) methyl-(2-methyl-4-o-tolyloxy-pyrimidin-5-yl)-carbamic acid tert.-butyl ester in 25 ml CH$_2$Cl$_2$ 2 ml trifluoracetic acid was added and the reaction mixture stirred for 2 hrs. at 40°. The reaction mixture was poured into ice-water and the pH of the solution adjusted to 10 with 1N NaOH solution. The aqueous phase was extracted three times with 80 ml CH$_2$Cl$_2$. The combined organic layers were dried (Na$_2$SO$_4$), filtered and evaporated to give 0.95 g (72%) methyl-(2-methyl-4-o-tolyloxy-pyrimidin-5-yl)-amine as a light yellow solid, MS (EI): 229.2 (M$^+$).

d) 2-(3,5-Bis-trifluoromethyl-phenyl)-N-methyl-N-(2-methyl-4-o-tolyloxy-pyrimidin 5-yl)-isobutyramide To a solution of 0.4 g (1.74 mol) 2-(3,5-bis-trifluoromethyl-phenyl)-N-methyl-N-(2-methyl-4-o-tolyloxy-pyrimidin-5-yl)-isobutyramide and 0.6 ml (3.49 mmol) N-ethyldiisopropylamine in 15 ml CH$_2$Cl$_2$ a solution of 0.78 g (2.44 mmol) 2-(3,5-bis-trifluormethyl-phenyl)-2-methyl-propionyl chloride in 5 ml CH$_2$Cl$_2$ was added and the reaction mixture stirred for 12 hrs at RT. The reaction mixture was poured into 50 ml 0.5 N NaOH-solution. The phases were separated and the aqueous phase three times extracted with 80 ml CH$_2$Cl$_2$. The combined organic layers were dried (Na$_2$SO$_4$), filtered and evaporated. The residue was purified by chromatography (SiO$_2$, CH$_2$Cl$_2$/MeOH 40:1) to give 0.82 g (94%) 2-(3,5-bis-trifluoromethyl-phenyl)-N-methyl-N-(2-methyl-4-o-tolyloxy-pyrimidin-5-yl)-isobutyramide as a white foam, MS (ISP): 511.1 (M+H)$^+$.

EXAMPLE 73

2-(3,5-Bis-trifluoromethyl-phenyl)-N-methyl-N-(2-phenyl-4-o-tolyloxy-pyrimidin-5-yl)-isobutyramide In an analougous manner to that described in Examle 72 a) there was obtained from 2-phenyl-4-o-tolyloxy-pyrimidine-5-carboxylic acid, diphenylphosphorylazide and t-butanol (2-phenyl-4-o-tolyloxy-pyrimidin-5-yl)-carbamic acid tert.-butyl ester, which was methylated with methyliodide and than deprotected with trifluoracetic acid according to Example 72 b) c). The resulting methyl-(2-phenyl-4-o-tolyloxy-pyrimidin-5-yl)-amine was treated with 2-(3,5-bis-trifluormethyl-phenyl)-2-methyl-propionyl chloride as described in Example 72 e) to give 2-(3,5-bis-trifluoromethyl-phenyl)-N-methyl-N-(2-phenyl-4-o-tolyloxy-pyrimidin-5-yl)-isobutyramide as a white foam, MS (ISP): 574.1 (M+H)$^+$.

EXAMPLE A

Tablets of the following composition are manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

EXAMPLE C

Suppositories of the following composition are manufactured:

|  | mg/supp. |
| --- | --- |
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

What is claimed is:

1. A compound of the formula:

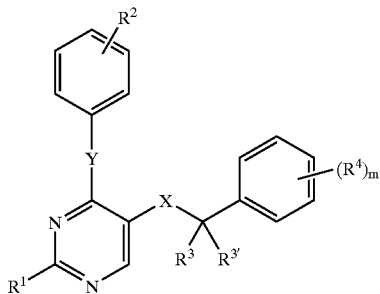

wherein
R$^1$ is lower alkyl, lower alkoxy, pyridinyl, pyrimidinyl, phenyl, —S-lower alkyl, —S(O)$_2$-lower alkyl, —N(R$^a$)—(CH$_2$)$_n$—N(R$^b$)$_2$, —O—(CH$_2$)$_n$—N(R$^c$)$_2$, —N(R$^d$)$_2$,
or a cyclic tertiary amine of the group

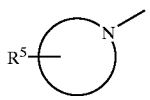

having no or one additional heteroatom, selected from N, O or S, said cyclic tertiary amine being connected directly to a pyrimidine ring of formula 1 or connected to said pyrimidine ring of formula 1 via the linker —O(CH$_2$)$_n$—;
R$^2$ is hydrogen, lower alkyl, lower alkoxy, halogen or trifluoromethyl;
R$^3$/R$^{3'}$ are, independently from each other, hydrogen or lower alkyl;
(R$^4$)m are, independently from each other in the case where m is not 0 or 1, halogen, trifluoromethyl or lower alkoxy;
R$^5$ is hydrogen or lower alkyl;
R, R$^a$, R$^b$, R$^c$, R$^d$, R$^e$, R$^f$ are, independently from each other, hydrogen or lower alkyl;
X is N(R$^f$)C(O)—;
Y is —O—, —S—, —SO$_2$—, - or —N(R)—;
n is 1,2,3 or 4; and
m is 0,1 or 2;

or a pharmaceutically acceptable acid addition salt thereof.

2. A compound of formula I according to claim 1, wherein R$^1$ is a cyclic tertiary amine of the group

3. A compound of formula I according to claim 2, wherein R$^1$ is —O—(CH$_2$)$_n$-cyclic tertiary amine of the group

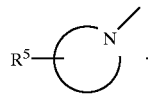

4. A compound of formula I according to claim 1, wherein R$^1$ is the group —O—(CH$_2$)—NR$^c$$_2$.

5. A compound of formula I according to claim 1, wherein X is —N(CH$_3$)C(O)— and Y is —O—.

6. A compound of formula I according to claim 5, wherein R$^1$ is —S-lower alkyl.

7. A compound of formula I according to claim 5, which is
2-(3,5-bis-trifluoromethyl-phenyl)-N-methyl-N-(2-methylsulfanyl-4-o-tolyloxy-pyrimidin-5-yl)-isobutyramide,
2-(3,5-bis-trifluoromethyl-phenyl)-N-[4-(4-fluoro-phenoxy)-2-methylsulfanyl-pyrimidin-5-yl]-N-methyl-isobutyramide or
2-(3,5-bis-trifluoromethyl-phenyl)-N-[4-(2-chloro-phenoxy)-2-methylsulfanyl-pyrimidin-5-yl]-N-methyl-isobutyramide.

8. A compound of formula I according to claim 5, wherein R$^1$ is a cyclic tertiary amine of the group

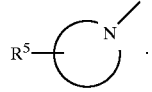

9. A compound of formula I according to claim 8, which is
2-(3,5-bis-trifluoromethyl-phenyl)-N-methyl-N-(2-morpholin-4-yl-4-o-tolyloxy-pyrimidin-5-yl)-isobutyramide,
2-(3,5-bis-trifluoromethyl-phenyl)-N-methyl-N-[2-(4-methyl-piperazin-1-yl)-4-o-tolyloxy-pyrimidin-5-yl]-isobutyramide,
2-(3,5-bis-trifluoromethyl-phenyl)-N-methyl-N-(2-piperazin-1-yl-4-o-tolyloxy-pyrimidin-5-yl)-isobutyramide,
2-(3,5-bis-trifluoromethyl-phenyl)-N-[4-(4-fluoro-phenoxy)-2-(4-methyl-piperazin-1-yl)-pyrimidin-5-yl]-N-methyl-isobutyramide,
2-(3,5-bis-trifluoromethyl-phenyl)-N-[4-(4-fluoro-phenoxy)-2-piperazin-1-yl-pyrimidin-5-yl]N-methyl-isobutyramide,
2-(3,5-bis-trifluoromethyl-phenyl)-N-[4-(2-chloro-phenoxy)-2-morpholin-4-yl-pyrimidin-5-yl]-N-methyl-isobutyramide,
2-(3,5-bis-trifluoromethyl-phenyl)-N-[4-(2-chloro-phenoxy)-2-(4-methyl-piperazin-1-yl)-pyrimidin-5-yl]-N-methyl-isobutyramide or
2-(3,5-Bis-trifluoromethyl-phenyl)-N-[4-(2-chloro-phenoxy)-2-piperazin-1-yl-pyrimidin-5-yl]-N-methyl-isobutyramide.

10. A compound of formula I according to claim 5, wherein R$^1$ is —N(R$^a$)(CH$_2$)$_n$NR$^b$$_2$.

11. A compound of formula I according to claim 10, which is
2-(3,5-bis-trifluoromethyl-phenyl)-N-[2-(2-dimethylamino-ethylamino)-4-o-tolyloxy-pyrimidin-5-yl]-N-methyl-isobutyramide or
2-(3,5-bis-trifluoromethyl-phenyl)-N-[2-(2-dimethylamino-ethylamino)-4-(4-fluoro-phenoxy)-pyrimidin-5-yl]-N-methyl-isobutyramide.

12. A compound of formula I according to claim 5, wherein $R^1$ is a —O—$(CH_2)_n$-cyclic tertiary amine of the group

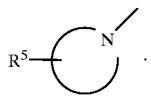

13. A compound of formula I according to claim 12, which is
2-(3,5-bis-trifluoromethyl-phenyl)-N-methyl-N-[2-(2-morpholin-4-yl-ethoxy)-4-o-tolyloxy-pyrimidin-5-yl]-isobutyramide,
2-(3,5-bis-trifluoromethyl-phenyl)-N-[4-(2-chloro-phenoxy)-2-(2-morpholin-4-yl-ethoxy)-pyrimidin-5-yl]-N-methyl-isobutyramide.

14. A compound of formula I according to claim 5, wherein $R^1$ is —O—$(CH_2)_n NR^c_2$.

15. A compound of formula I according to claim 14, which is
2-(3,5-bis-trifluoromethyl-phenyl)-N-[2-(2-dimethylamino-ethoxy)-4-o-tolyloxy-pyrimidin-5-yl]-N-methyl-isobutyramide,
2-(3,5-bis-trifluoromethyl-phenyl)-N-[2-(3-dimethylamino-propoxy)-4-o-tolyloxy-pyrimidin-5-yl]-N-methyl-isobutyramide,
2-(3,5-bis-trifluoromethyl-phenyl)-N-[2-(2-dimethylamino-ethoxy)-4-(4-fluoro-phenoxy)-pyrimidin-5-yl]-N-methyl-isobutyramide,
2-(3,5-bis-trifluoromethyl-phenyl)-N-[2-(3-dimethylamino-propoxy)-4-(4-fluoro-phenoxy)-pyrimidin-5-yl]-N-methyl-isobutyramide,
2-(3,5-bis-trifluoromethyl-phenyl)-N-[2-(2-dimethylamino-ethoxy)-4-(2-chloro-phenoxy)-pyrimidin-5-yl]-N-methyl-isobutyramide or
2-(3,5-bis-trifluoromethyl-phenyl)-N-[2-(3-dimethylamino-propoxy)-4-(2-chloro-phenoxy)-pyrimidin-5-yl]-N-methyl-isobutyramide.

16. A medicament containing an effective amount of a compound of formula I according to claim 1 and a pharmaceutically acceptable excipient.

17. A compound of formula I according to claim 1 wherein X is —N($R^f$)C(O)— wherein $R^f$ is lower alkyl, Y is —O— and $R^2$ is lower alkyl.

18. A compound of formula 1 according to claim 17 wherein the compound is
2-(3,5-bis-trifluoromethyl-phenyl)-N-(2-methanesulfonyl-4-o-tolyloxy-pyrimidin-5-yl)-N-methyl-isobutyramide;
2-(3,5-bis-trifluoromethyl-phenyl)-N-methyl-N-(2-methyl-4-o-tolyloxy-pyrimidin-5-yl)-isobutyramide; or
2-(3,5-bis-trifluoromethyl-phenyl)-N-methyl-N-(2-phenyl-4-o-tolyloxy-pyrimidin-5-yl)-isobutyramide.

19. A compound of formula I according to claim 1 wherein X is —N($R^f$)C(O)— wherein $R^f$ is lower alkyl, Y is —O— and $R^2$ is halogen.

20. A compound of formula 1 according to claim 19 wherein the compound is
2-(3,5-bis-trifluoromethyl-phenyl)-N-[4-(4-fluoro-phenoxy)-2-methanesulfonyl-pyrimidin-5-yl]-N-methyl-isobutyramide;
2-(3,5-bis-trifluoromethyl-phenyl)-N-[4-(4-fluoro-phenoxy)-2-(4-methyl-piperazin-1-yl)-pyrimidin-5-yl]-N-methyl-isobutyramide;
2-(3,5-bis-trifluoromethyl-phenyl)-N-[4-(4-fluoro-phenoxy)-2-(2-morpholin-4-yl-ethoxy)-pyrimidin-5-yl]-N-methyl-isobutyramide;
2-(3,5-bis-trifluoromethyl-phenyl)-N-[4-(2-chloro-phenoxy)-2-methanesulfonyl-pyrimidin-5-yl]-N-methyl-isobutyramide;
2-(3,5-bis-trifluoromethyl-phenyl)-N-[4-(2-chloro-phenoxy)-2-morpholin-4-yl-pyrimidin-5-yl]-N-methyl-isobutyramide; or
2-(3,5-bis-trifluoromethyl-phenyl)-N-[4-(2-chloro-phenoxy)-2-piperazin-1-yl-pyrimidin-5-yl]-N-methyl-isobutyramide.

* * * * *